(12) United States Patent
Tashiro et al.

(10) Patent No.: US 10,993,608 B2
(45) Date of Patent: May 4, 2021

(54) ENDOSCOPE SYSTEM AND CONTROL METHOD

(71) Applicant: OLYMPUS CORPORATION, Tokyo (JP)

(72) Inventors: Junichi Tashiro, Higashimurayama (JP); Hideyuki Kugimiya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/896,633

(22) Filed: Jun. 9, 2020

(65) Prior Publication Data

US 2020/0297202 A1 Sep. 24, 2020

Related U.S. Application Data

(63) Continuation of application No. PCT/JP2018/032421, filed on Aug. 31, 2018.

(30) Foreign Application Priority Data

Dec. 13, 2017 (JP) .............................. JP2017-238629

(51) Int. Cl.
*A61B 1/045* (2006.01)
*A61B 1/00* (2006.01)
(Continued)

(52) U.S. Cl.
CPC .......... *A61B 1/045* (2013.01); *A61B 1/00009* (2013.01); *A61B 1/00016* (2013.01);
(Continued)

(58) Field of Classification Search
CPC . A61B 1/045; A61B 1/00009; A61B 1/00016; A61B 1/00045; A61B 1/00059;
(Continued)

(56) References Cited

U.S. PATENT DOCUMENTS

| 9,324,145 | B1* | 4/2016 | Cherevatsky ............. G06T 7/42 |
| 2013/0281987 | A1 | 10/2013 | Maeda |
| 2013/0307951 | A1* | 11/2013 | Ono ..................... H04N 5/2355 |
| | | | 348/68 |

FOREIGN PATENT DOCUMENTS

| JP | 2002-125983 A | 5/2002 |
| JP | 2002-336184 A | 11/2002 |

(Continued)

OTHER PUBLICATIONS

International Search Report dated Nov. 20, 2018 issued in PCT/JP2018/032421.

*Primary Examiner* — Shan E Elahi
(74) *Attorney, Agent, or Firm* — Scully, Scott, Murphy & Presser, P.C.

(57) ABSTRACT

An endoscope system includes: a processor configured to perform image processing on endoscopic image data, the processor being connectable with multiple peripherals, the processor being configured to receive an input of a first audio command; a terminal device configured to wirelessly communicate with the processor and receive an input of a second audio command; a setting circuit configured to, in a case where the processor and the terminal device can communicate with each other, make a setting such that the first audio command that is receivable by the processor and the second audio command that is receivable by the terminal device differ from each other at least partly; and a first communication controller configured to, when the first audio command or the second audio command serves as an instruction to record the endoscopic image data, transmit the endoscopic image data to the terminal device.

12 Claims, 13 Drawing Sheets

(51) Int. Cl.
   *G06F 3/16*      (2006.01)
   *H04N 5/232*     (2006.01)
   *A61B 5/1172*    (2016.01)
   *A61B 8/12*      (2006.01)
   *H04N 5/225*     (2006.01)

(52) U.S. Cl.
   CPC ...... *A61B 1/00045* (2013.01); *A61B 1/00059* (2013.01); *G06F 3/16* (2013.01); *H04N 5/23203* (2013.01); *A61B 5/1172* (2013.01); *A61B 8/12* (2013.01); *H04N 2005/2255* (2013.01)

(58) Field of Classification Search
   CPC ......... A61B 5/1172; A61B 8/12; A61B 8/467; A61B 8/565; A61B 1/00006; A61B 1/00039; G06F 3/16; H04N 5/23203; H04N 2005/2255; H04N 9/045; H04N 5/232; G02B 23/24
   USPC .......................................................... 348/74
   See application file for complete search history.

(56) References Cited

FOREIGN PATENT DOCUMENTS

| | | |
|---|---|---|
| JP | 2003-164464 A | 6/2003 |
| WO | WO 2013/061857 A1 | 5/2013 |

\* cited by examiner

ENDOSCOPE SYSTEM AND CONTROL METHOD

CROSS-REFERENCE TO RELATED APPLICATION

This application is a continuation of PCT International Application No. PCT/JP2018/032421 filed on Aug. 31, 2018, which designates the United States, incorporated herein by reference, and which claims the benefit of priority from Japanese Patent Application No. 2017-238629, filed on Dec. 13, 2017, incorporated herein by reference.

BACKGROUND

1. Technical Field

The disclosure relates to an endoscope system that displays image data obtained by inserting an endoscope into a subject and capturing in-vivo images of the subject and to a control method.

2. Related Art

As for recent endoscope systems, a technique to control multiple electronic devices according to an audio input has been known (refer to Japanese Laid-open Patent Publication No. 2002-336184). In the technology, when control on the electronic devices is executed according to an audio command that is input via an audio input unit, notifying about a request for approval of the execution prevents an incorrect operation caused by the audio input.

SUMMARY

In some embodiments, an endoscope system includes: processor configured to perform image processing on endoscopic image data that is acquired by an endoscope that performs in-vivo observation on a subject, the processor being connectable with multiple peripherals, the processor being configured to receive an input of a first audio command serving as an instruction to drive any one of the peripherals based on audio data that is generated by an audio input circuit receiving an input of sound; a terminal device configured to wirelessly communicate with the processor and receive an input of a second audio command serving as an instruction to drive any one of the peripherals using sound; a setting circuit configured to, in a case where the processor and the terminal device can communicate with each other, make a setting such that the first audio command that is receivable by the processor and the second audio command that is receivable by the terminal device differ from each other at least partly; and a first communication controller configured to, when the first audio command or the second audio command serves as an instruction to record the endoscopic image data, transmit the endoscopic image data to the terminal device.

In some embodiments, provided is a control method that is executed by an endoscope system including a processor configured to perform image processing on endoscopic image data that is acquired by an endoscope that performs in-vivo observation on a subject, the processor being connectable with multiple peripherals, the processor being configured to receive an input of a first audio command serving as an instruction to drive any one of the peripherals based on audio data that is generated by an audio input circuit receiving an input of sound; and a terminal device configured to wirelessly communicate with the processor and receive an input of a second audio command serving as an instruction to drive any one of the peripherals using sound. The control method includes: in a case where the processor and the terminal device can communicate with each other, making a setting such that the first audio command that receivable by the processor and the second audio command that is receivable by the terminal device differ from each other at least partly; and when the first audio command or the second audio command serves as an instruction to record the endoscopic image data, transmit the endoscopic image data to the terminal device.

The above and other features, advantages and technical and industrial significance of this disclosure will be better understood by reading the following detailed description of presently preferred embodiments of the disclosure, when considered in connection with the accompanying drawings.

DETAILED DESCRIPTION

An endoscope system including an endoscope that captures in-vivo images of an internal cavity of a subject, such as a patient, and displays the in-vivo images will be exemplified and described as a mode for carrying out the disclosure ("embodiment" below). The embodiment does not limit the disclosure. In the description of the drawings, the same components are denoted by the same reference numbers.

First Embodiment

Configuration of Endoscope System

Figure 1:
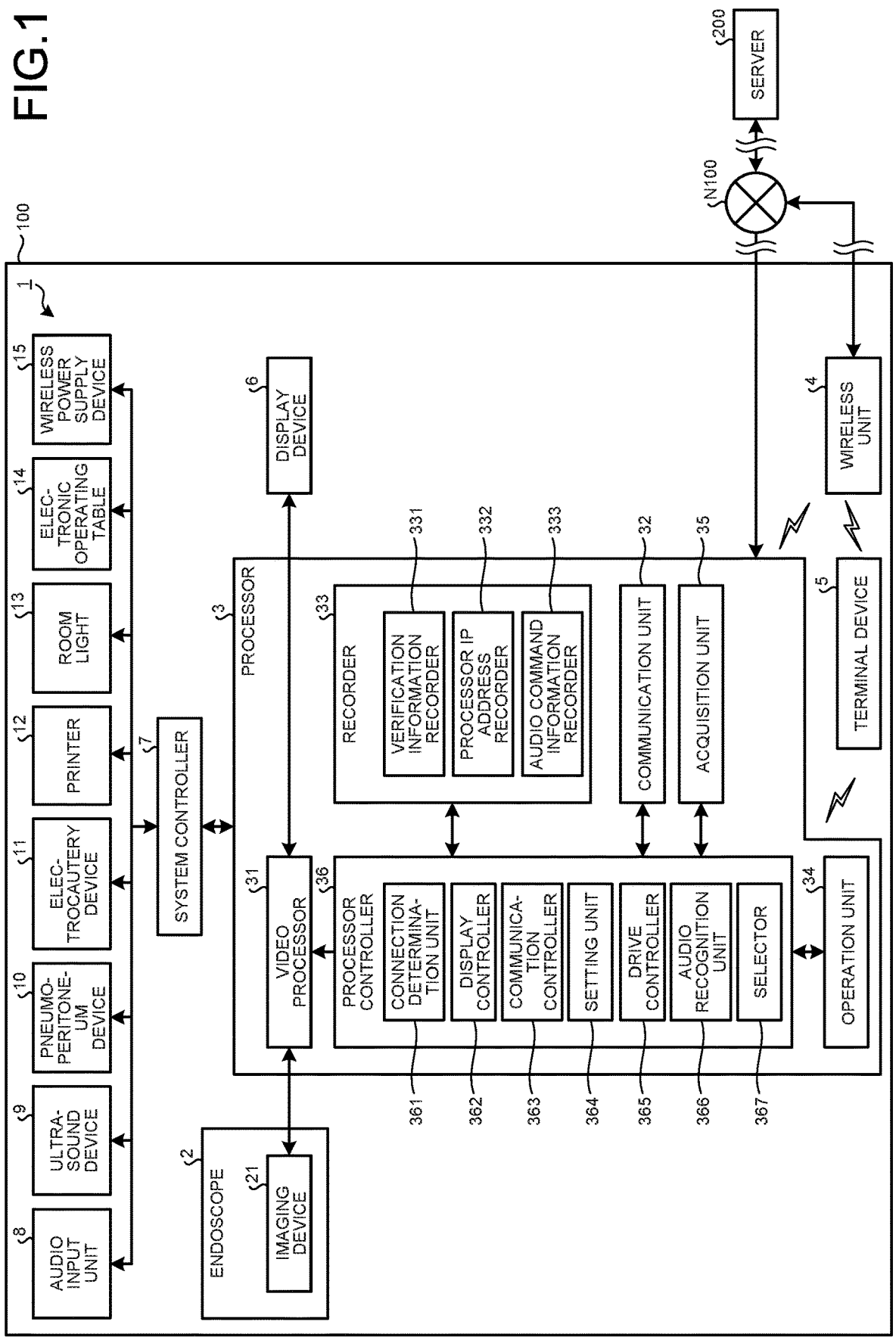
FIG. 1 is a block diagram illustrating a functional configuration of an endoscope system according to a first embodiment of the disclosure.

FIG. 1 is a block diagram illustrating a functional configuration of an endoscope system according to a first embodiment of the disclosure. An endoscope system 1 illustrated in FIG. 1 is used when health professionals including at least a doctor perform an endoscopic surgery, an endoscopic examination, or an endoscopic treatment on a subject, such as a patient, in an operation room 100 in a hospital. The endoscope system 1 includes an endoscope 2, a processor 3, a wireless unit 4, a terminal device 5, a display device 6, a system controller 7, an audio input unit 8, an ultrasound device 9, a pneumoperitoneum device 10, an electrocautery device 11, a printer 12, a room light 13, an electronic operating table 14, and a wireless power supply device 15.

First of all, a configuration of the endoscope 2 will be described. The endoscope 2 is inserted into the subject. The endoscope 2 is configured using a rigid endoscope or a flexible endoscope. Under the control of the processor 3, the endoscope 2 applies illumination light to the inside of the subject, captures in-vivo images of an area of the subject to which the illumination light is applied, generates endoscopic image data and then outputs the generated endoscopic image data to the processor 3. The endoscope 2 includes an imaging device 21 that captures in-vivo images of the subject and generates image data. The imaging device 21 is configured using an image sensor, such as a charge coupled device (CCD) or a complementary metal oxide semiconductor (CMOS), an A/C conversion circuit, etc. The endoscope 2 is connected to the processor 3 in a wireless or wired manner such that interactive communication can be performed in between. When transmitting the generated endoscopic image data wirelessly, the endoscope 2 may transmit the endoscopic image data sequentially to the processor 3 via the wireless unit 4 to be described below or may transmit the endoscopic image data sequentially to a server 200 that is set in the hospital and outside the operation room 100 via a network N100.

A configuration of processor 3 will be described. The processor 3 controls the endoscope 2, performs given processing on the endoscope image data that is sequentially input from the endoscope 2, sequentially outputs the processed endoscopic image data, and is connectable to multiple peripherals and is capable of, based on audio data that is generated by the audio input unit 8 that receives an input of sound, receiving an input of a first audio command giving an instruction to drive any one of the peripherals. The first audio command is configured of a command that makes it possible to operate all the peripherals. The processor 3 includes a video processor 31, a communication unit 32, a recorder 33, an operation unit 34, an acquisition unit 35, and a processor controller 36.

The video processor 31 performs given image processing on the endoscopic image data that is input from the endoscope 2 and outputs the processed endoscopic image data to the display device 6. The given image processing includes synchronization processing, demosaicing processing (when the imaging device 21 has a Bayer array), white balance adjustment processing, γ correction processing, chroma adjustment processing, and format conversion processing. The video processor 31 is configured using a field programmable gate array (FPGA), an application specific integrated circuit (ASIC), a graphics processing unit (GPU), etc.

The communication unit 32 is configured using a communication module and performs interactive communication with the terminal device 5 according to given communication standards. The communication unit 32 performs interactive communication with the terminal device 5 via the wireless unit 4 or performs interactive communication with the server 200 that is set in the hospital via the network N100. The given communication standards are Wi-Fi (Wireless Fidelity) (trademark) communication, Bluetooth (trademark) communication, Bluetooth Low Energy (trademark) communication (simply referred to as "BLE communication" below), or the like. For example, Wi-Fi assumes a local area network and, as for roles of devices, there is a relationship between an access point and a station and, as for a schematic connection process, there is a relationship in which the station is connected to a wireless network that is formed by the access point. In a rough connection sequence, first of all, the wireless unit 4 serving as an access point forms the wireless network and informs about a network identifier (SSID) of the network. Sequentially, the communication unit 32 of the processor 3 serving as the station searches for the network identifier (SSID) that is informed about and connects to a desired network (access point). A network with a large number of devices is assumed and the covered area wide and thus a strict identifying step is taken in consideration of the problem of interference. This may increase the time to establish connection. Note that, in data communication, it is possible to transmit or receive data at the timing of each of the access point and the station. The communication unit 32 may employ communication by 4G wireless communication other than Wi-Fi communication. Needless to say, the communication unit 32 may employ other communication, such as communication by 3G wireless communication, communication by 5G wireless communication, WiMax (Worldwide interoperability for Microwave Access) (trademark) communication, or infrared communication (IrDA (Infrared Data Association) (trademark)).

The recorder 33 records various programs to be executed by the processor 3, data being processed, the endoscopic image data, etc. The recorder 33 is configured using a flash memory, a synchronous dynamic random access memory (SDRAM), a memory card and a solid state drive (SSD), or the like. The recorder 33 includes a verification information recorder 331 that records a device address of a device authorized to perform interactive wireless communication with the processor 3 and connectability determination information, a processor IP address recorder 332 that records a processor IP address that identifies the processor 3, and an audio command information recorder 333 that records a template for recognizing the control content of an audio command based on audio data that is generated by the audio input unit 8. The verification information recorder 331 records multiple sets of operator identification information that identify operators of the endoscope 2 ("operator IDs" below), respectively, in association with levels according to which operating each of the peripherals is permitted.

The operation unit 34 receives inputs of various types of information on the endoscope system 1 and outputs the received information to the processor controller 36. The operation unit 34 is configured using, for example, switches, buttons, a touch panel, etc. The operation unit 34 receives an input of an operator ID that identifies a practitioner who performs treatment on the subject and outputs the operator ID to the processor controller 36.

The acquisition unit 35 acquires an operator ID that is set in an ID card of an operator of the endoscope 2 and outputs the operator ID to the processor controller 36. The operator ID includes an operator level representing an ID information level, a post, and a name. The operator level is information representing permission to operate each of the peripherals according to each level. For example, an operator level of an operating surgeon who is the operator (practitioner) is permitted to operate all the peripherals, an operator level of a doctor who is an assistant is permitted to operate part of the peripherals, for example, excluding the ultrasound device 9, the electrocautery device 11 and the electronic operating table 14, an operator level of an anesthesiologist is permitted to operate the pneumoperitoneum device 10, the printer 12, the room light 13 and the electronic operating table 14, an operator level of a scrub nurse is permitted to operate the printer 12 and the room light 13, and an operator level of a circulation nurse is permitted to operate the printer 12. The acquisition unit 35 is configured using, for example, a RFID reader or a communication module capable of Bluetooth communication.

The processor controller 36 controls each unit of the processor 3 and each device configuring the endoscope system 1. The processor controller 36 is configured using a central processing unit (CPU), etc. The processor controller 36 includes a connection determination unit 361, a display controller 362, a communication controller 363, a setting unit 364, a drive controller 365, an audio recognition unit 366, and a selector 367.

The connection determination unit 361 determines whether the terminal device 5 is a connection partner with which interactive communication can be performed based on a terminal device IP address and a result of verification that are transmitted from the terminal device 5.

The display controller 362 controls the display mode of the display device 6. Specifically, the display controller 362 causes the display device 6 to display the endoscopic image corresponding to the endoscopic image data on which the video processor 31 has performed the image processing. When interactive wireless communication between the processor 3 and the terminal device 5 is established, the display controller 362 causes the display device 6 to display information indicating that the processor 3 and the terminal device 5 can perform interactive wireless communication.

Based on the result of determination performed by the connection determination unit 361 and the result of verification that is transmitted from the terminal device 5, the communication controller 363 permits the terminal device 5 to communicate with the peripherals.

Based on the level that is assigned to a registered user corresponding to the result of verification that is transmitted from the terminal device 5 and the verification information that is recorded by the verification information recorder 331, the setting unit 364 sets multiple peripherals that are operable according to a second audio command of which input is received by the terminal device 5 via the system controller 7. Based on an operator ID that is acquired by the acquisition unit 35 and the verification information that is recorded in the verification information recorder 331, the setting unit 364 further sets multiple peripherals that are operable according to a first audio command of which input is received by the audio input unit 8 via the system controller 7.

Based on an audio command that is recognized by the audio recognition unit 366 to be described below or a request signal and an operation signal that are input from the terminal device 5 via the communication unit 32, the drive controller 365 controls the system controller 7 and thereby control driving the peripherals. When the setting unit 364 has not make a setting such that peripherals corresponding to the second audio command that is input from the terminal device 5 are operable, the drive controller disables the second audio command and does not execute control on the peripherals.

The audio recognition unit 366 refers to audio command information that is recorded in the audio command information recorder 333 and recognizes the content of an audio command based on audio data that is input from the audio input unit 8. Specifically, using the template representing a waveform of each audio command that is contained in the audio command information that is recorded in the audio command information recorder 333, the audio recognition unit 366 performs known pattern matching on the audio data and thus recognizes the content of an audio command (first audio command) representing driving any one of the peripherals and the control content and outputs the result of recognition to the drive controller 365. Based on the audio data and based on the voiceprints or feature values of the operator IDs that are registered previously, the audio recognition unit 366 may recognize and specify the operator who has input the sound to the audio input unit 8. The audio recognition unit 366 may recognize the audio command content with respect to audio data that is transmitted from the terminal device 5 via the communication unit 32.

In the case where the processor 3 and the terminal device 5 can communicate with each other, when the processor 3 receives inputs of the first audio command via the audio input unit 8 and the second audio command from the terminal device 5, the selector 367 selects a priority audio command to be prioritized. Specifically, when the processor 3 receives inputs of the first audio command and the second audio command from the terminal device 5, the selector 367 selects a priority audio command to be prioritized from the first audio command and the second audio command based on the level of the operator that is acquired by the acquisition unit 35 and the level of the user who uses the terminal device 5.

A configuration of the wireless unit 4 will be described. The wireless unit 4 is connected to the server 200 via the network N100 and is connected to the processor 3 and the terminal device 5 according to given communication standards such that the wireless unit 4 can interactively communicate with the processor 3 and the terminal device 5. The wireless unit 4 employs Wi-Fi communication. The wireless unit 4 is set around the processor 3 or on a wall in the operation room 100.

A configuration of the terminal device 5 will be described. The terminal device interactively communicates with the processor 3 according to given communication standards and receives the endoscopic image data that is generated by the endoscope 2 and case image data from the server 200 via the wireless unit 4 and displays the data. The terminal device 5 is capable of receiving an input of the second audio command giving an instruction to drive any one of the peripherals by sound. The second audio command is configured of a command that makes it possible to operate a peripheral that does not directly relate to the operation. The detailed configuration of the terminal device 5 will be described below.

A configuration of the display device 6 will be described. Under the control of the display controller 362, the display device 6 displays the image corresponding to the image data that is input from the video processor 31 and various types of information on the endoscope system 1. The display device 6 is configured using a liquid crystal or organic electro luminescence (EL) display monitor, a speaker that outputs sound to the outside, etc.

The system controller 7 is connected to the processor 3 in a wired or wireless manner and individually controls each of the audio input unit 8, the ultrasound device 9, the pneumoperitoneum device 10, the electrocautery device 11, the printer 12, the room light 13, the electronic operating table 14, and the wireless power supply device 15 according to an instruction signal that is input from the processor 3. Any one of the audio input unit 8, the ultrasound device 9, the pneumoperitoneum device 10, the electrocautery device 11, the printer 12, the room light 13, the electronic operating table 14, and the wireless power supply device 15 to be referred to is simply referred to as a "peripheral". The system controller 7 is connected to each of the peripherals in a wired or wireless manner. The system controller 7 is configured using the CPU, a flash memory, etc.

Under the control of the system controller 7, the audio input unit 8 picks up sound that is output from a sound source or a speaker, converts the sound into an analog audio signal (electric signal), performs A/D conversion processing and gain adjustment processing on the audio signal, generates digital audio data, and outputs the digital audio data to the processor 3 via the system controller 7. The audio input unit 8 is configured using any one of a unidirectional microphone, an omnidirectional microphone and a bidirectional microphone, an A/D conversion circuit and a signal processing circuit. The audio input unit 8 is worn on the operator of the endoscope. Needless to say, the audio input unit 8 may be arranged in the operation room 100 other than being worn on the operator or may be worn on a nurse or an assistant other than the operator. The single audio input unit 8 need not be used and the number of audio input units may be changed as appropriate. For example, audio input units corresponding in number to the health professionals who are in the operation room 100 including the operator may be arranged.

The ultrasound device 9 is connected to the endoscope 2 and, under the control of the system controller 7, transmits and receives ultrasound via an ultrasound transducer that is arranged at the distal end of the endoscope 2. The ultrasound device 9 outputs ultrasound image data based on the ultrasound that is received via the endoscope 2 to the system controller 7. The ultrasound device 9 may generate ultrasound image data on the subject via a dedicated ultrasound probe.

Under the control of the system controller 7, the pneumoperitoneum device 10 sends a pneumoperitoneum gas, such as carbon dioxide, into the subject.

Under the control of the system controller 7, the electrocautery device 11 drives the electrocautery by applying a given voltage to the electrocautery.

Under the control of the system controller 7, the printer 12 outputs an image corresponding to the image data that is input from the processor 3.

The room light 13 includes a plurality of room lights that are arranged in the operation room 100 and, under the control of the system controller 7, applies light to the subject and the operation room 100 in a given illuminance. The room light 13 is configured using a light emitting diode (LED) lamp, a light adjustment switch, etc.

As for the electronic operating table 14, the subject is arranged on an operating table. Under the control of the system controller 7, the electronic operating table 14 is moved vertically and horizontally to change the position and posture of the subject. The electronic operating table 14 is configured using an operating table that is movable vertically and horizontally and a driver, such as a motor, that drives the operating table.

Under the control of the system controller 7, the wireless power supply device 15 wirelessly supplies power to the terminal device 5. The wireless power supply device 15 is configured using any one of an electromagnetic induction system, a magnetic resonance system, an electric field coupling system, and a radio transmission reception system.

The server 200 is set outside the operation room 100 and in the hospital and records the endoscopic image data that is transmitted from the processor 3 or the terminal device 5 via the network N100 a patient ID that identifies the patient in association with each other. On receiving an image request signal requesting case image data and endoscopic image data via the network N100 or the wireless unit 4, the server 200 transmits the case image data and the endoscopic image data to the processor 3 or the terminal device 5 that transmits the image request signal. The endoscopic image data herein includes video data and still image data (captured image data).

Configuration of Terminal Device

Figure 2:
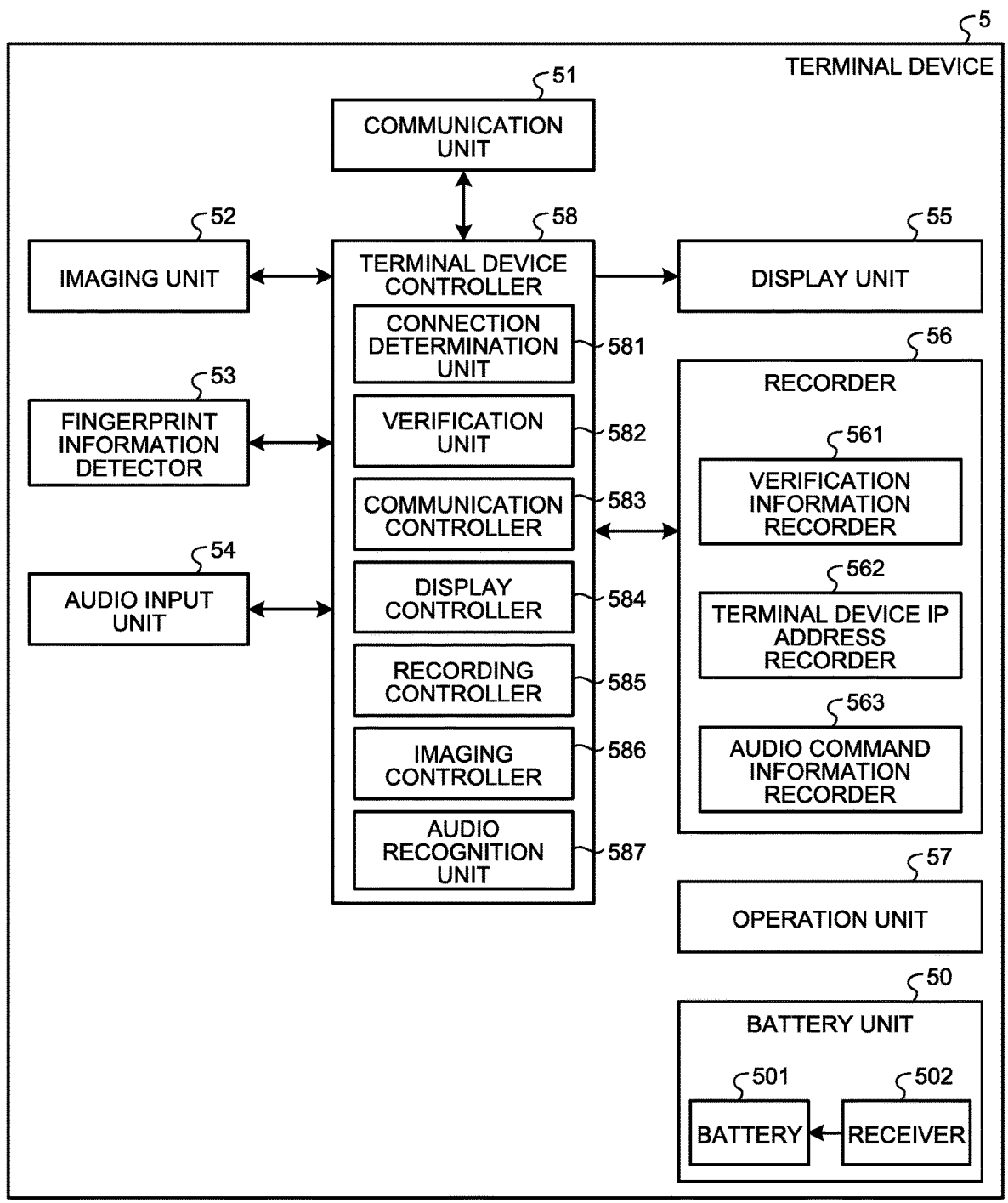
FIG. 2 is a block diagram illustrating a functional configuration of a terminal device according to the first embodiment of the disclosure.

The detailed configuration of the terminal device referred to in FIG. 1 will be described. FIG. 2 is a block diagram illustrating a functional configuration of the terminal device 5.

The terminal device 5 illustrated in FIG. 2 includes a battery unit 50, a communication unit 51, an imaging unit 52, a fingerprint information detector 53, an audio input unit 54, a display unit 55, a recorder 56, an operation unit 57, and a terminal device controller 58.

The battery unit 50 includes a battery 501 that supplies power to each unit configuring the terminal device 5 and a receiver 502 that receives electromagnetic waves that are supplied from the wireless power supply device 15, converts the electromagnetic waves into a current, and supplies the current to the battery 501.

The communication unit 51 is configured using a communication module and performs interactive communication with the processor 3 according to the given communication standards. The communication unit 51 interactively communicates with the server 200 via the wireless unit 4 and the network N100 in the hospital. As the given communication standards, Wi-Fi communication is assumed. The communication unit 51 may employ communication by 4G wireless communication other than Wi-Fi communication. Needless to say, the communication unit 51 may employ another type of communication, such as Bluetooth communication, BLE communication, communication by 30 wireless communication, communication by 5G wireless communication, WiMAX communication or infrared communication.

Under the control of the terminal device controller 58, the imaging unit 52 captures an image of the user of the terminal device 5 and generates image data and then outputs the image data to the terminal device controller 58. The imaging unit 52 is configured using an image sensor, such as a CCD or a CMOS, an image processing engine that is implemented using A/D conversion processing, a FPGA or a GPU, etc. An infrared lamp capable of emitting infrared light and an image sensor in which pixels capable of capturing images of the infrared light that is applied by the infrared lamp may be arranged in the imaging unit 52 to acquire irregularities on the surface of the face of the user.

The fingerprint information detector 53 detects fingerprint information on the fingers of the user that externally touches the fingerprint information detector 53 and outputs the result of detection to the terminal device controller 58. The fingerprint information detector 53 configured using a fingerprint sensor. The fingerprint information detector 53 is configured using a fingerprint sensor. The fingerprint information detector 53 may employ a slide system other than a pressing system. The fingerprint information detector 53 may detect veins of the user other than fingerprints.

Under the control of the terminal device controller 58, the audio input unit 54 picks up the sound that is output from a sound source or a speaker, converts the sound into an analog audio signal (electric signal), performs A/D conversion processing and gain adjustment processing on the audio signal, generates digital audio data, and outputs the digital audio data to the terminal device controller 58. The audio input unit 54 is configured using any one of a unidirectional microphone, an omnidirectional microphone and a bidirectional microphone, an A/D conversion circuit, a signal processing circuit, etc.

The display unit 55 displays image data that is input from the terminal device controller 58 and various types of information. The display unit 55 is configured using a liquid crystal or organic EL display panel.

The recorder 56 records various programs to be executed by the terminal device 5, data being processed, and image data. The recorder 56 is configured using a flash memory, a SSD, a memory card, etc. The recorder 56 includes a verification information recorder 561, a terminal device IP address recorder 562 that records a terminal device IP address that identifies the terminal device 5, and an audio command information recorder 563 that records a template for recognizing the control content of an audio command based on audio data that is input from the audio input unit 54.

The operation unit 57 receives an input of an instruction signal corresponding to an operation from the user. The operation unit 57 is configured using a touch panel, buttons, switches, etc.

The terminal device controller 58 generally controls the components of the terminal device 5. The terminal device controller 58 analyzes the audio data that is input from the audio input unit 54, generates an audio command based on the result of the analysis, and transmits the audio command to the processor 3. The terminal device controller 58 is configured using the CPU, etc. The terminal device controller 58 includes a connection determination unit 581, a verification unit 582, a communication controller 583, a display controller 584, a recording controller 585, an imaging controller 586, and an audio recognition unit 587.

Based on the verification information that is received by the communication unit 51 from the processor 3, the connection determination unit 581 determines whether the processor 3 is a connection partner with which interactive wireless communication can be performed.

The verification unit 582 verifies whether the user of the terminal device 5 is the registered user who is registered previously. Specifically, the verification unit 582 performs verification in which any one of a face image of the user of the terminal device 5, biological information of the user, and gesture information on the user is acquired. For example, the verification unit 582 determines whether the feature of the face image of the user in the image corresponding to the image data that is generated by the imaging unit 52 matches the feature of the registered user that is recorded in the recorder 56.

Based on the result of determination by the connection determination unit 581 and the result of verification by the verification unit 582, the communication controller 583 permits interactive wireless communication between the processor 3 and the terminal device 5 or interactive wireless communication between the network N100 and the terminal device 5.

The display controller 584 controls the display mode of the display unit 55. Specifically, the display controller 584 causes the display unit 55 to display an endoscopic image corresponding to endoscopic image data and a case image corresponding to case image data.

The recording controller 585 causes the recorder 56 to record a patient round time contained in schedule information that is acquired by the communication controller 583 and the endoscopic image data in association with each other.

When the verification unit 582 verifies that the user is the registered user, the imaging controller 586 enables the imaging function of the imaging unit 52 by the user of the terminal device 5.

The audio recognition unit 587 refers to the audio command information that is recorded in the audio command information recorder 563 and recognizes the content of the audio command based on the audio data that is input from the audio input unit 54. Specifically, using the template representing a waveform of each audio command contained in the audio command information that is recorded in the audio command information recorder 563, the audio recognition unit 587 performs known pattern matching on the audio data and thus recognizes the content of an audio command representing driving any one of the peripherals and the control content and outputs the result of recognition to the communication controller 583.

Process Executed by Processor

Figure 3:
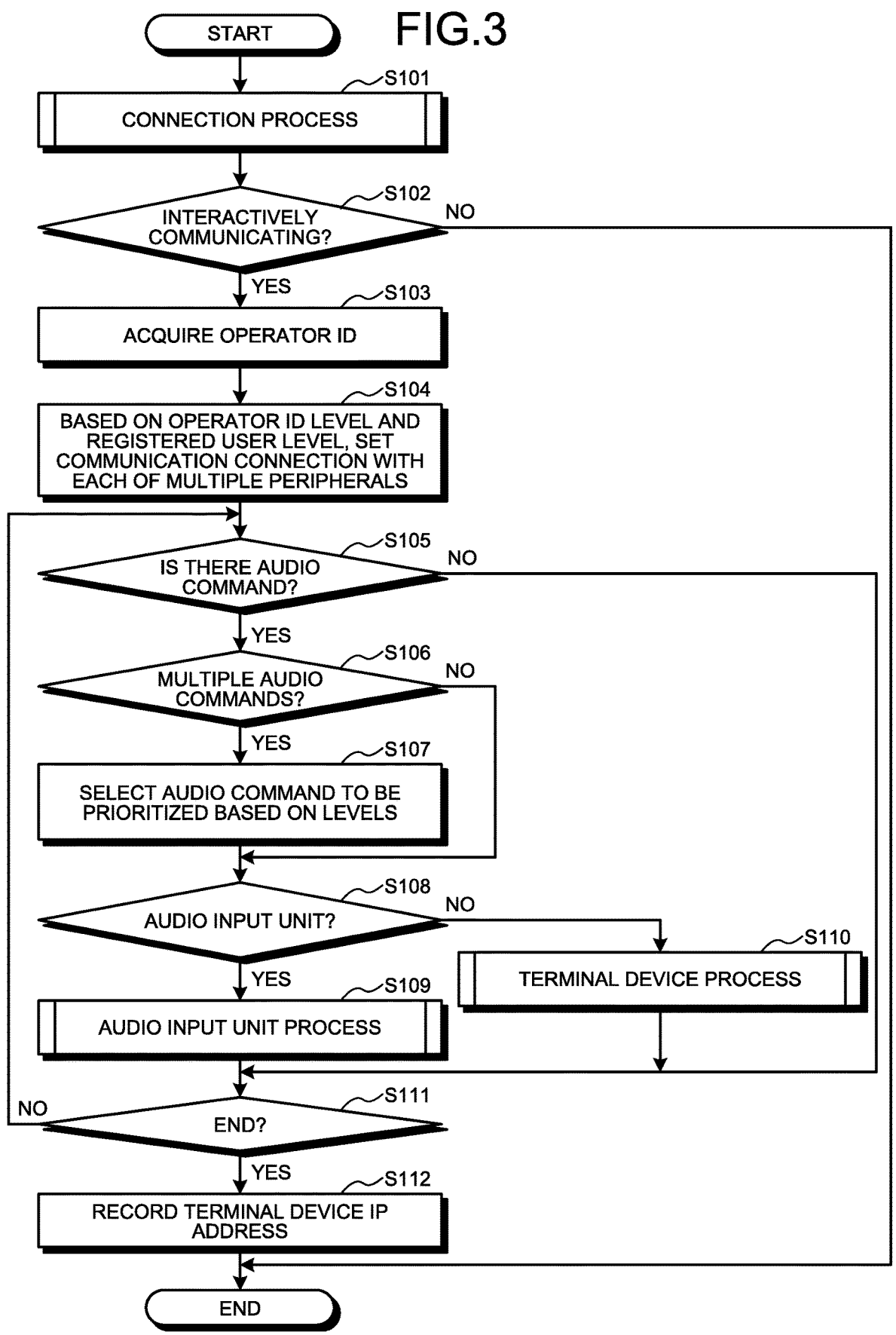
FIG. 3 is a flowchart illustrating an overview of a process that is executed by a processor according the first embodiment of the disclosure.

A process that is executed by the processor 3 will be described. FIG. 3 is a flowchart illustrating an overview of the process that is executed by the processor 3.

As illustrated in FIG. 3, first of all, the processor 3 executes a connection process of establishing a connection for interactively communicating with the terminal device 5 (step S101). After step S101, the processor 3 moves to step S102 to be described below.

Connection Process

Figure 4:
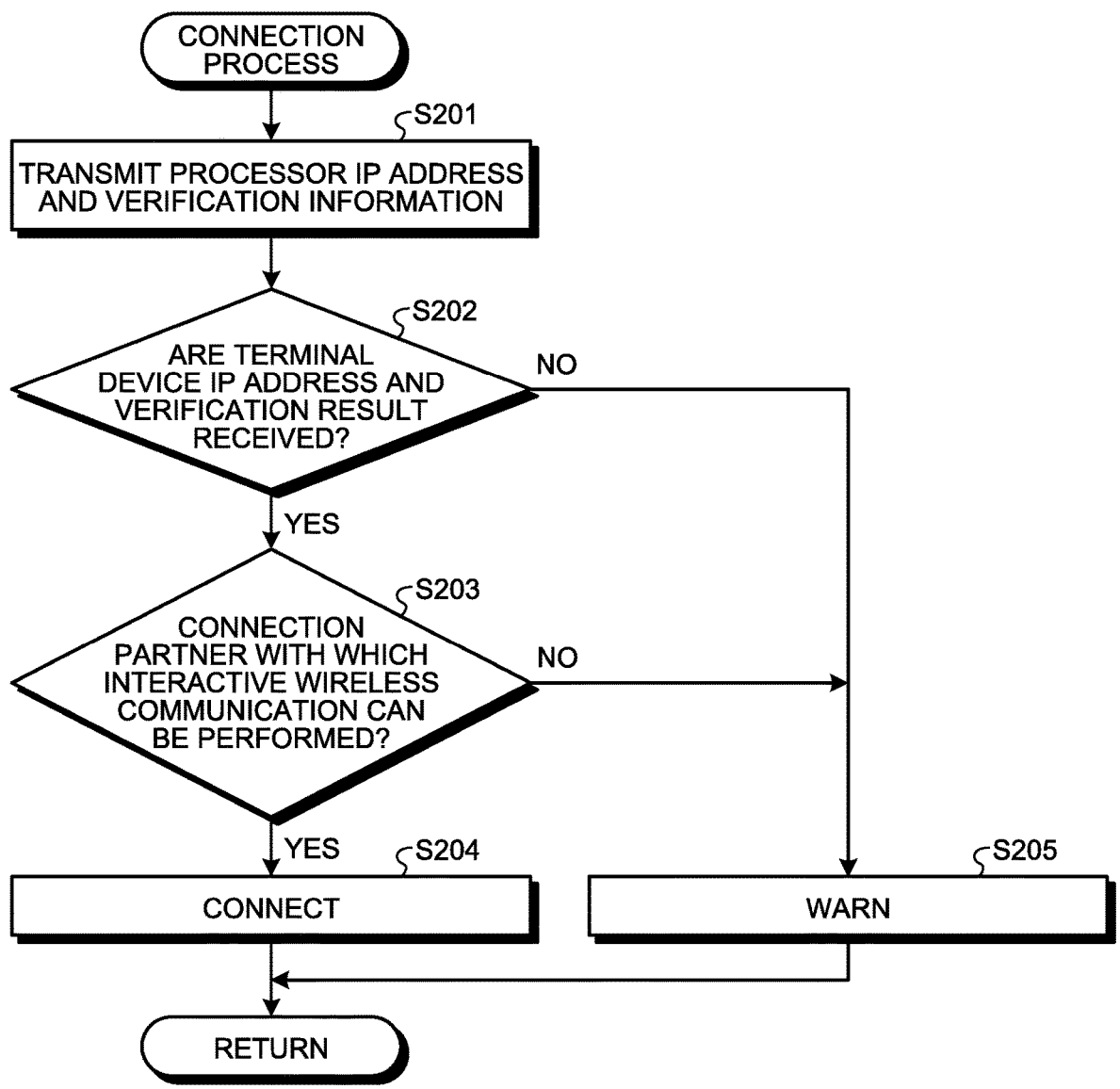
FIG. 4 is a flowchart illustrating an overview of a connection process in FIG. 3.

An overview of the connection process that is referred to at step S101 in FIG. 3 will be described. FIG. 4 is a flowchart illustrating an overview of the connection process.

As illustrated in FIG. 4, first of all, the communication controller 363 transmits the processor IP address (SSID) and the verification information to the terminal device 5 via the communication unit 32 (step S201). The verification information is information for requesting a result of verification performed by the verification unit 582, which is a verification result functioning as a password for interactive wireless communication of the terminal device 5.

Sequentially, on receiving the terminal device IP address and the result of verification performed by the verification unit 582 from the terminal device 5 via the communication unit 32 (YES at step S222), the processor 3 moves to step S203 to be described below. On the other hand, when the terminal device IP address and the result of verification performed by the verification unit 582 are not received from the terminal device 5 via the communication unit 32 (NO at step S202), the processor 3 moves to step S205.

At step S203, based on the terminal device IP address and the result of verification performed by the verification unit 582 that are received by the communication unit 32, the connection determination unit 361 determines whether the terminal device 5 is a connection partner with which interactive wireless communication can be performed (step S203). Specifically, the connection determination unit 361 determines whether the terminal device IP address and the result of verification performed by the verification unit 582 that are received by the communication unit 32 match the verification information that is recorded in the verification information recorder 331. While it is determined that the terminal device 5 is a connection partner with which interactive wireless communication can be performed when the terminal device IP address and the verification result match the verification information, it is determined that the terminal device 5 is not a connection partner with which interactive wireless communication can be performed when the terminal device IP address and the verification result do not match the verification information. When the connection determination unit 361 determines that the terminal device 5 is a connection partner with which interactive wireless communication can be performed (YES at step S203), the processor 3 moves to step S204 to be described below. On the other hand, when the connection determination unit 361 determines that the terminal device 5 is not a connection partner with which interactive wireless communication can be performed (NO at step S203), the processor 3 moves to step S205 to be described below.

At step S204, the communication controller 363 connects the processor 3 and the terminal device 5 such that the processor 3 and the terminal device 5 can interactively communicate with each other. Accordingly, the processor 3 enters a state where the processor 3 can interactively communicate with the terminal device 5. In this case, the display controller 362 may cause the display device 6 to display that interactive wireless communication can be performed between the processor 3 and the terminal device 5. In other words, the display controller 362 functions as an informing unit. After step S204, the processor 3 returns to the main routine in FIG. 3.

At step S205, the display controller 362 causes the display device 6 to display a warning that the terminal device 5 is not a connection partner with which interactive wireless communication can be performed. The display controller 362 causes the display device 6 display a warning that the terminal device 5 is not a connection partner with which interactive wireless communication can be performed; however, alternatively, for example, a warning that the terminal device 5 is not a connection partner with which interactive wireless communication can be performed may be informed about using a speaker, which is not illustrated in the drawings, or the like. In other words, the display controller 362 functions as an informing unit that informs that interactive wireless communication between the processor 3 and the terminal device 5 cannot be performed. After step S205, the processor 3 returns to the main routine in FIG. 3.

FIG. 3 will be referred back to continue describing step S102 and the following steps.

At step S102, when the processor 3 and the terminal device 5 are interactively communicating with each other (YES at step S102), the acquisition unit 35 acquires an operator ID (step S103).

Sequentially, based on an operator ID level that is acquired by the acquisition unit 35 and the level that is assigned to the registered user corresponding to the verification result that is received from the terminal device 5, the setting unit 364 sets communication connection with each of multiple peripherals that are operable according to an audio command of which input is received by each of the audio input unit 8 and the terminal device 5 via the system controller 7 (step S104). Specifically, when the operator ID level and the level of the registered user are the level of doctor, the setting unit 364 makes a setting such that all the peripherals are operable via the terminal device 5 are operable. On the other hand, when the operator ID level and the level of the registered user are the level of nurse, the setting unit 364 sets only given peripherals for peripherals operable via the terminal device 5, for example, makes a setting such that peripherals not related to the operation, more specifically, the printer 12, the room light 13, the wireless power supply device 15, etc., are operable. Needless to say, based on the operator ID level and the level of the registered user, the setting unit 364 may finely set peripherals operable via the audio input unit 8 and the terminal device 5.

Sequentially, in the case where an audio command comes from the audio input unit 8 or the terminal device 5 (YES at step S105), when there are multiple commands within a given time (for example, one to two seconds) (YES at step S106), the selector 367 selects an audio command to be prioritized based on the levels (step S107). Specifically, the selector 367 compares the operator ID level of the audio input unit 8 and the level of the registered user and preferentially selects the audio command of the higher level.

Sequentially, when an audio command is input from the audio input unit 8 (YES at step S108), the processor 3 moves to step S109 to be described below. On the other hand, when no audio command is input from the audio input unit 8 (NO at step S108), the processor 3 moves to step S110 to be described below.

At step S109, the processor 3 executes an audio input unit process of driving peripherals according to the audio command that is input from the audio input unit 8. After step S109, the processor 3 moves to step S111 to be described below.

Audio Input Unit Process

Figure 5:
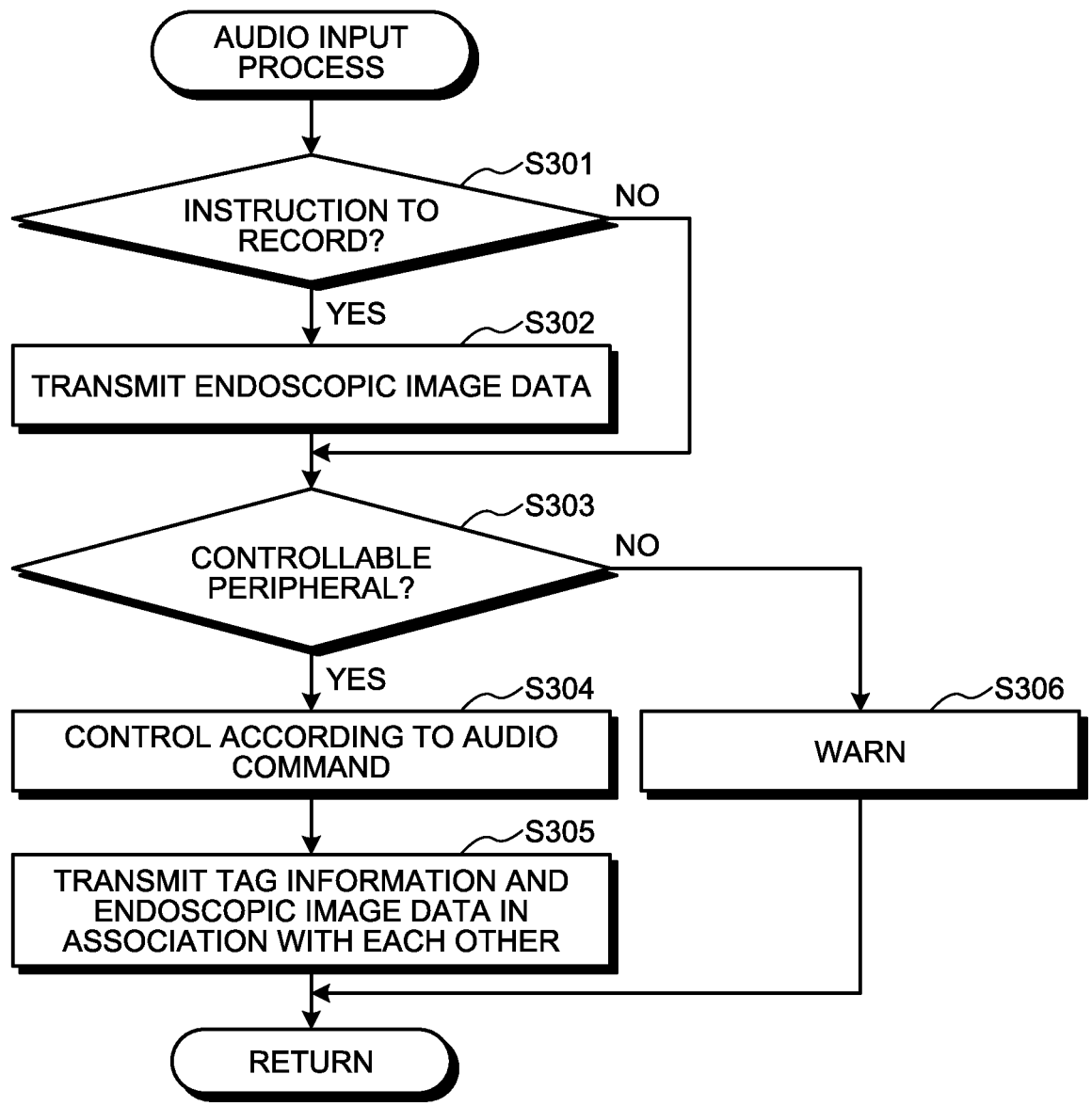
FIG. 5 is a flowchart illustrating an overview of an audio input unit process in FIG. 3.

An overview of the audio input unit process referred to at step S109 in FIG. 3 will be described. FIG. 5 is a flowchart illustrating an overview of the audio input unit process.

As illustrated in FIG. 5, first of all, when the audio command that is input from the audio input unit 8 serves as an instruction to record the endoscopic image data (YES at step S301), the communication controller 363 transmits the endoscopic image data to the terminal device 5 via the communication unit 32 (step S302). After step S302, the processor 3 moves to step S303 described below.

At step S301, when the audio command that is input from the audio input unit 8 does not serve as an instruction to record the endoscopic image data (NO at step S301), the processor 3 moves to step S303 to be described below.

At step S303, when a peripheral to be controlled according to the audio command that is input from the audio input unit 8 is a controllable peripheral that is set by the setting unit 364 (YES at step S303), the drive controller 355 controls the peripheral according to the control content corresponding to the audio command that is recognized by the audio recognition unit 366 (step S304).

Sequentially, the communication controller 363 transmits tag information on the content of the audio command and the endoscopic image data in association with each other to the terminal device 5 via the communication unit 32 (step S305). After step S305, the processor 3 returns to the main routine in FIG. 3.

At step S303, when the peripheral that is controlled according to the audio command that is input from the audio input unit 8 is not a controllable peripheral that is set by the setting unit 364 (NO at step S303), the display controller 362 causes the display device 6 to display a warning that the peripheral is uncontrollable (step S306). After step S306, the processor 3 returns to the main routine in FIG. 3.

FIG. 3 will be referred back to continue describing step S110 and the following steps.

At step S110, the processor 3 executes a terminal device process of driving a peripheral according to an audio command that is input from the terminal device 5. After step S110, the processor 3 moves to step S111 to be described below.

Terminal Device Process

Figure 6:
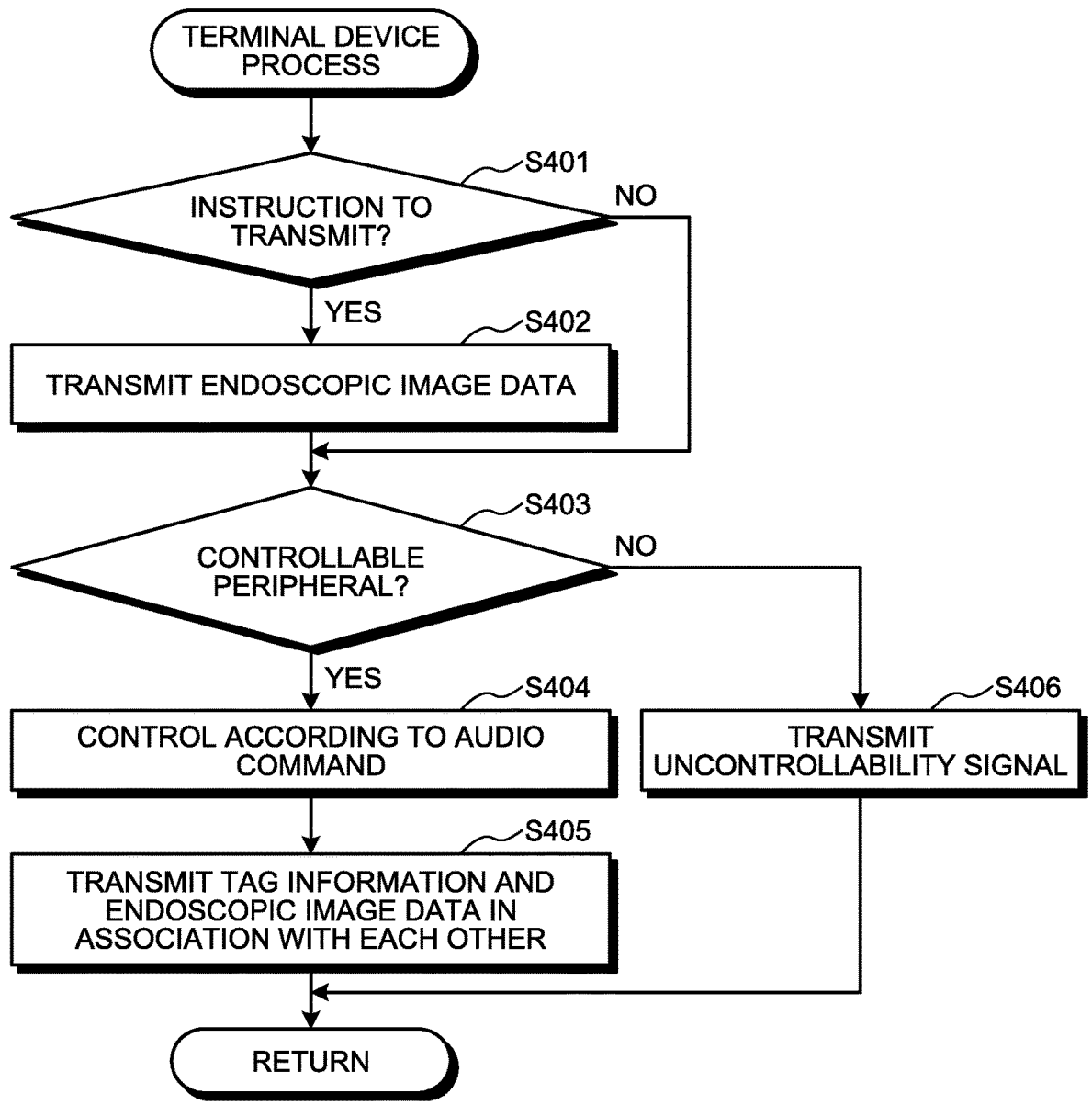
FIG. 6 is a flowchart illustrating an overview of a terminal device process in FIG. 3.

An overview of the terminal device process referred to at step S110 in FIG. 3 will be described. FIG. 6 is a flowchart illustrating an overview of the terminal device process.

As illustrated in FIG. 6, first of all, when the audio command that is input from the terminal device 5 serves as an instruction to transmit the endoscopic image data (YES at step S401), the communication controller 363 transmits the endoscopic image data to the terminal device 5 via the communication unit 32 (step S402). After step S402, the processor 3 moves to step S403 to be described below.

At step S402, when the audio command that is input from the terminal device 5 does not serve as an instruction to transmit the endoscopic image data (NO at step S401), the processor 3 moves to step S403 to be described below.

At step S403, when a peripheral to be controlled according to the audio command that is input from the terminal device 5 is a controllable peripheral that is set by the setting unit 364 (YES at step S403), the drive controller 365 controls the peripheral according to the control content corresponding to the audio command that is recognized by the audio recognition unit 366 (step S404).

Sequentially, the communication controller 363 transmits tag information on the content of the audio command and the endoscopic image data in association with each other to the terminal device 5 via the communication unit 32 (step S405). After step S405, the processor 3 returns to the main routine in FIG. 3.

At step S403, when the peripheral that is controlled. according to the audio command that is input from the terminal device 5 is not a controllable peripheral that is set by the setting unit 364 (NO at step S403), the communication controller 363 transmits an uncontrollability signal indicating that the peripheral is not operable to the terminal device 5 via the communication unit 32 (step S406). After step S406, the processor 3 returns to the main routine in FIG. 3.

FIG. 3 will be referred back to continue describing step S111 and the following steps.

At step S111, when an instruction signal of an instruction to end is input from the operation unit 34 or the terminal device 5 (YES at step S111), the processor 3 moves to step S112 to be described below. On the other hand, when no instruction signal of an instruction to end is input from the operation unit 34 or the terminal device 5 (NO at step S111), the processor 3 returns to step S105 described above.

At step S102, when the processor 3 and the terminal device 5 are not communicating with each other (NO at step S102), the processor 3 ends the process.

At step S105, when no audio command comes from the audio input unit 8 or the terminal device 5 (NO at step S105), the processor 3 moves to step S111.

At step S106, when there are not multiple commands within the given time (NO at step S106), the processor 3 moves to step S108.

At step S112, the communication controller 363 records the terminal device IP address of the terminal device 5 in the recorder 33. This promptly enables communication between the processor 3 and the terminal device 5 when the terminal device 5 is powered on in the operation room 100. After step S112, the processor 3 ends the process.

Process executed by Terminal Device

Figure 7:
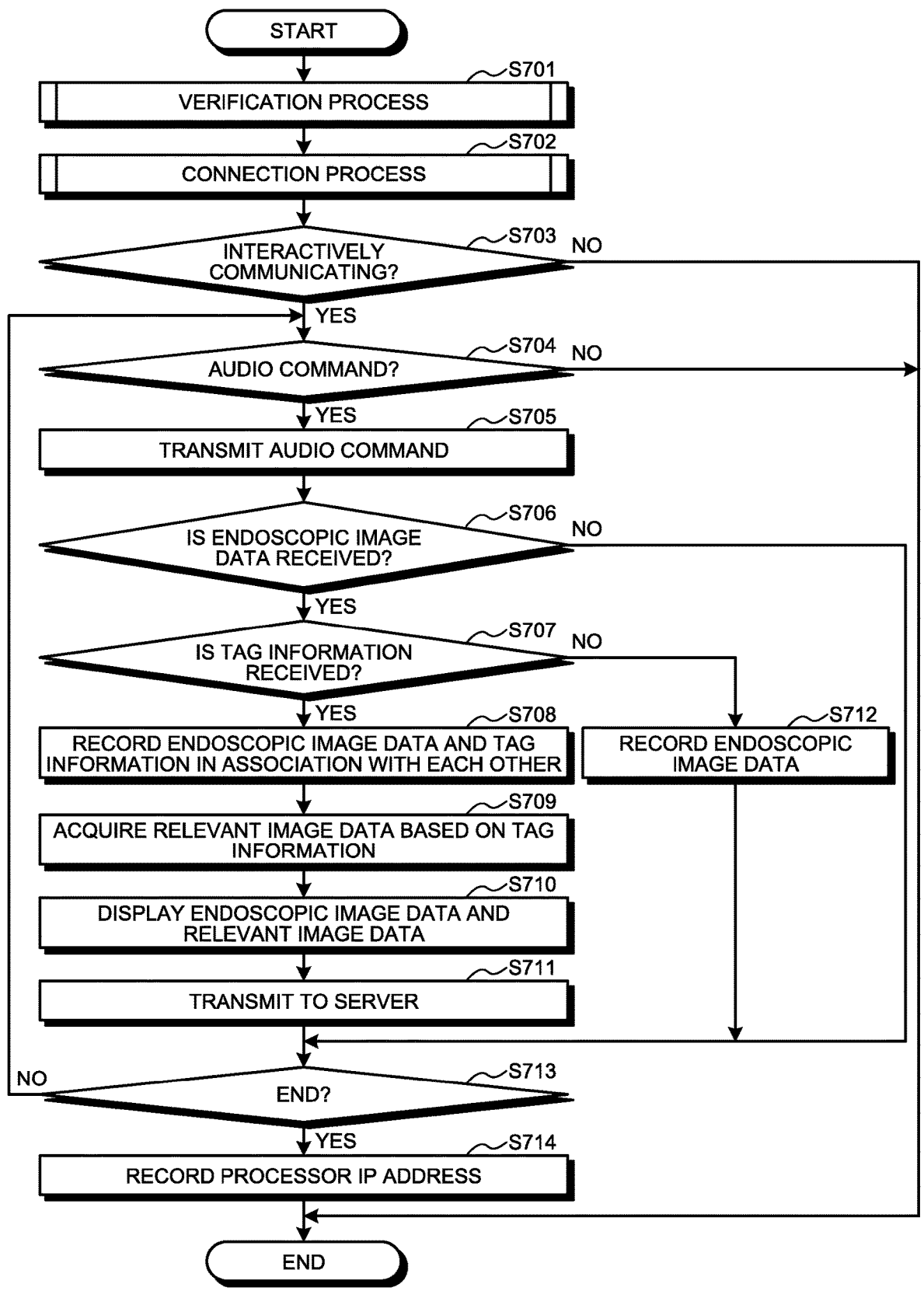
FIG. 7 is a flowchart illustrating an overview of a process that is executed by the terminal device according to the first embodiment of the disclosure.

A process that is executed by the terminal device 5 will be described. FIG. 7 is a flowchart illustrating an overview of the process that is executed by the terminal device 5.

As illustrated in FIG. 7, first of all, the terminal device 5 executes a verification process of verifying whether the user of the terminal device 5 is the registered user who can operate the terminal device 5 (step S701). After step S701, the terminal device 5 moves to step S702 to be described below.

Verification Process

Figure 8:
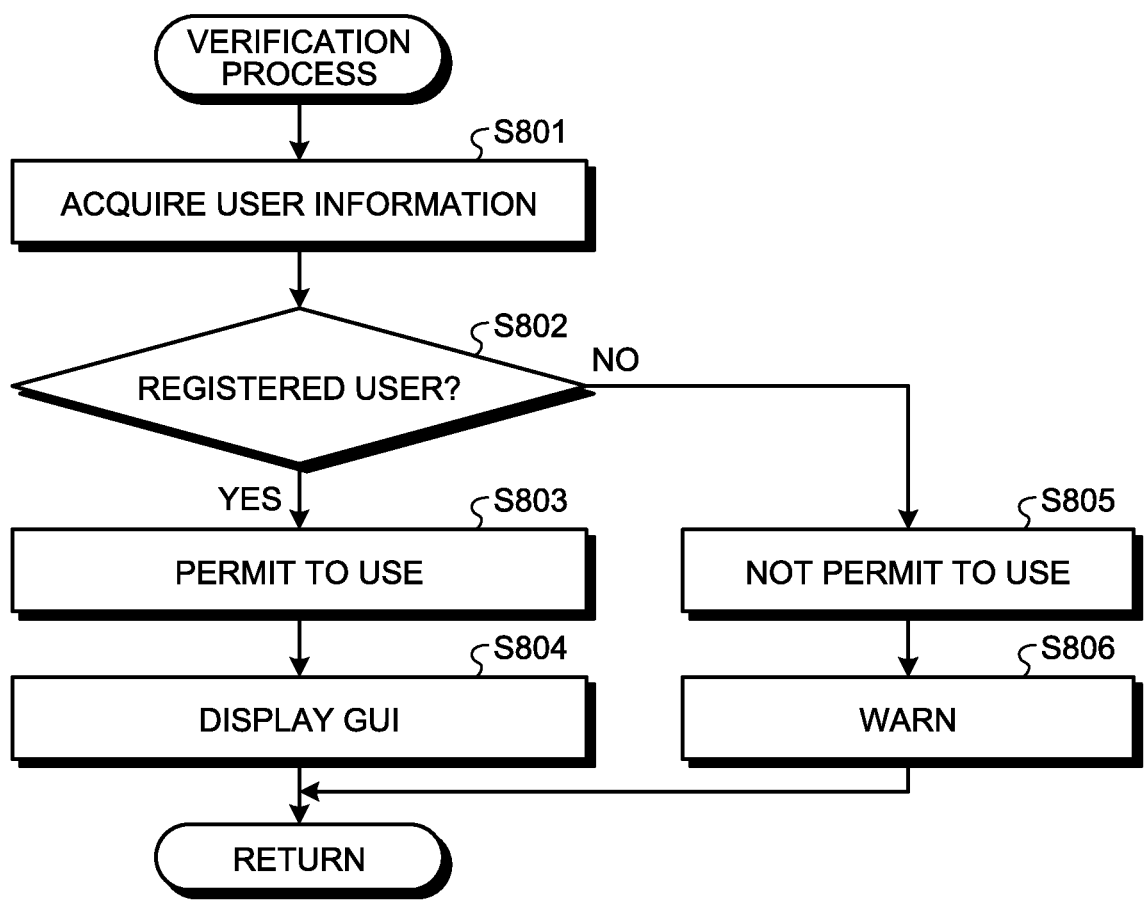
FIG. 8 is a flowchart illustrating an overview of a verification process in FIG. 7.

Details of the verification process referred to at step S701 in FIG. 7 will be described. FIG. 8 is a flowchart illustrating an overview of the verification process.

As illustrated in FIG. 8, the verification unit 582 acquires information on the user of the terminal device 5 (step S801). Specifically, the verification unit 582 acquires any one of image data obtained by the imaging unit 52 by capturing an image of the user of the terminal device 5, fingerprint information on the user that is detected by the fingerprint information detector 53, and audio data that is generated by the audio input unit 54 from a corresponding one of the imaging unit 52, the fingerprint information detector 53, and the audio input unit 54.

Sequentially, based on information on the user of the terminal device 5 and the verification information that is recorded in the verification information recorder 561, the verification unit 582 determines whether the user is the registered user (step S802). Specifically, based on the image data that is generated by the imaging unit 52 and verification information that is recorded in the verification information recorder 561, the verification unit 582 verifies whether the user is the registered user. More specifically, the verification unit 582 determines whether the feature of the face of the user in the image corresponding to the image data that is generated by the imaging unit 52 and the feature of the face of the registered user contained in the verification information that is recorded in the verification information recorder 561 have a given matching degree. While the verification unit 582 verifies that the user is the registered user when the features have the given matching degree, and the verification unit 582 verifies that the user is not the registered user when the features do not have the given matching degree. The verification unit 582 verifies whether the user is the registered user based on the fingerprint information that is detected by the fingerprint information detector 53 and the verification information that is recorded in the verification information recorder 561. More specifically, the verification unit 582 determines whether the feature of the fingerprint information on the user that is detected by the fingerprint information detector 53 and the feature of the fingerprint information on the registered user contained in the verification information that is recorded in the verification information recorder 561 have a given matching degree. While the verification unit 582 verifies that the user is the registered user when the features have the given matching degree, the verification unit 582 verifies that the user is not the registered user when the features do not have the given matching degree. The verification unit 582 further verifies whether the user is the registered user based on the audio data that is generated by the audio input unit 54 and the verification information that is recorded in the verification information recorder 561. More specifically, the verification unit 582 determines whether the feature of the voice print of the audio data that is generated by the audio input unit 54 and the feature of the voice print of the registered user contained in the verification information that is recorded in the verification information recorder 561 have a given matching degree.

While the verification unit 582 verifies that the user is the registered user when the features have the given matching degree, the verification unit 582 verifies that the user is not the registered user when the features do not have the given matching degree. The verification unit 582 determines whether the gesture information on the user in the image corresponding to the image data that is generated by the imaging unit 52 and the gesture information contained in the verification information that is recorded in the verification information recorder 561 have a given matching degree. While the verification unit 582 verifies that the user is the registered user when the sets of gesture information have the given matching degree, the verification unit 582 verifies that the user is not the registered user when the sets of gesture information do not have the given matching degree. The gesture information herein refers to, for example, the number of blinks of the user, the shape of the mouth, the moves of the face, the moves of the hands, etc. When the verification unit 582 determines that the user of the terminal device 5 is the registered user (YES at step S802), the verification unit 582 permits the user to use the terminal device 5 (step S803).

The display controller 584 causes the display unit 55 to display a GUI capable of receiving operational inputs of the user, or the like (step S804). While the display controller 584 causes the display unit 55 to display a GUI capable of receiving operational inputs of the user, or the like; however, alternatively, the display controller 584 may inform that use of the terminal device 5 is permitted using a speaker not illustrated in the drawings, or the like. In other words, the display controller 584 functions as an informing unit that informs that interactive wireless communication between the processor 3 and the terminal device 5 or interactive communication between the network N100 and the terminal device 5 can be performed. After step S804, the terminal device 5 returns to the above-described main routine in FIG. 7.

At step S802, when the verification unit 582 determines that the user of the terminal device 5 is not the registered user (NO at step S802), the verification unit 582 does not permit the user to use the terminal device 5 (step S805).

The display controller 584 keeps the display unit 55 from displaying or causes the display unit 55 to display a warning (step S806). The display controller 584 keeps the display unit 55 from displaying or causes the display unit 55 to display a warning; however, alternatively, a warning may be output using a speaker not illustrated in the drawings, or the like. After step S806, the terminal device 5 returns to the above-described main routing in FIG. 7.

FIG. 7 will be referred back to continue describing step S702 and the following steps.

At step S702, the terminal device 5 executes a connection process for performing interactive communication with the processor 3 (step S702). After step S702, the terminal device 5 moves to step S703 to be described below.

Connection Process

Figure 9:
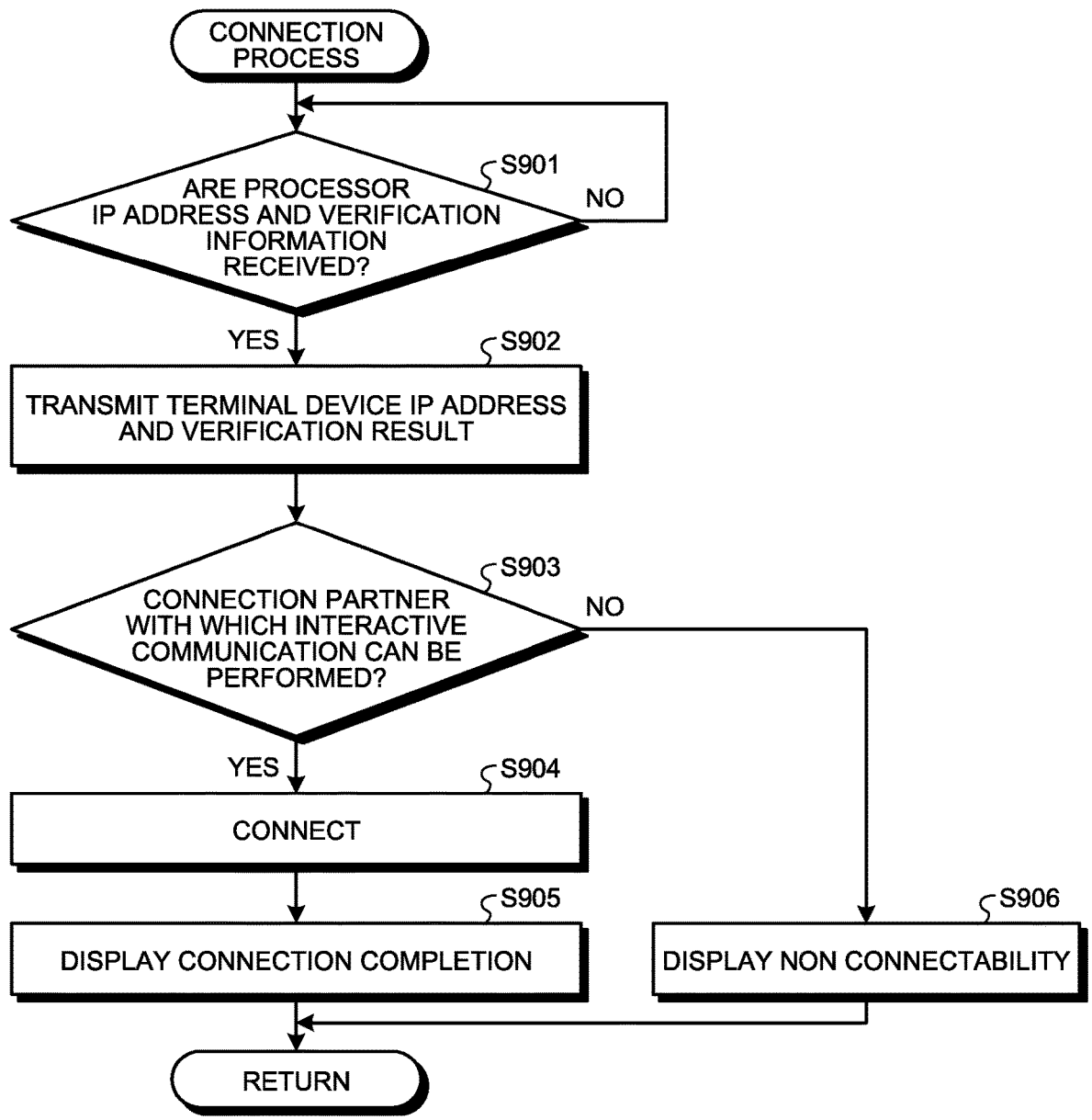
FIG. 9 is a flowchart illustrating an overview of a connection process in FIG. 7.

Details of the connection process referred to at step S702 in FIG. 7 will be described. FIG. 9 is a flowchart illustrating details of the connection process.

As illustrated in FIG. 9, first of all, the connection determination unit 581 determines whether the processor IP address (SSID) and the verification information are received from the processor 3 via the communication unit 51 (step S901). The verification information herein refers to information for requesting the result of verification performed by the verification unit 582, which is a verification result functioning as a password for interactive wireless communication with the processor 3. When the processor IP address (SSID) is received from the processor 3, the display controller 584 may cause the display unit 55 to display information on the processor IP address. In this case, en the display unit 55 displays multiple addresses, the user preferably selects a desired address via the operation unit 57. When the connection determination unit 581 determines that the processor IP address and the verification information are received from the processor 3 via the communication unit 51 (YES at step S901), the terminal device 5 moves to step S902 to be described below. On the other hand, when the connection determination unit 581 determines that the processor IP address and the verification information are not received from the processor 3 via the communication unit 51 (NO at step S901), the terminal device 5 performs this determination at given intervals (for example, every 10 seconds).

The communication controller 583 causes the communication unit 51 to transmit, to the processor 3, the terminal device IP address that is recorded in the terminal device IP address recorder 562 that is recorded in the recorder 56 and the result of verification performed by the verification unit 582 (step S902). In this case, the communication controller 583 causes the communication unit 51 to transmit the terminal device IP address and the verification result to an access point (the SSID of the processor 3 or the SSID of the wireless unit 4) that is selected previously by the user via the operation unit 57. In the first embodiment, the access point is the processor 3 or the wireless unit 4. Alternatively, the terminal device 5 may serve as the access point. In this case, the communication controller 583 may transmit a terminal device IP address (SSID) indicating that the terminal device 5 is within a given area, such as a communication area of Wi-Fi, via the communication unit 51.

At step S903, the connection determination unit 581 determines whether the processor IP address that is received by the communication unit 51 is a connection partner with which the terminal device 5 can interactively communicate (step S903). Specifically, the connection determination unit 581 determines whether the processor IP address is a processor IP address (SSID) that is selected by the user via the operation unit 57. When the connection determination unit 581 determines that the processor IP address that is received by the communication unit 51 is a connection partner with which the terminal device 5 can communicate interactively (YES at step S903), the terminal device 5 moves to step S904 to be described below. On the other hand, when the connection determination unit 581 determines that the processor IP address that is received by the communication unit 51 is not a connection partner with which the terminal device 5 can communicate interactively (NO at step S903), the terminal device 5 moves to step S906 to be described below.

At step S904, the communication controller 583 connects the processor 3 and the terminal device 5 such that the processor 3 and the terminal device 5 can communicate interactively. Accordingly, the terminal device 5 enters a state where the terminal device 5 can interactively communicate with the processor.

The display controller 584 causes the display unit 55 to display connection completion indicating that connecting with the processor 3 has completed (step S905). Accordingly, the user is able to instinctively know that the terminal device 5 enters a state where the terminal device 5 can interactively communicate with the processor 3. After step S905, the terminal device 5 returns to the main routine in FIG. 7. The display controller 584 causes the display unit 55 to display the connection completion; however, the embodiment is not limited thereto. For example, a speaker (not illustrated in the drawings) may be used to make an output indicating that connecting with the processor 3 has completed or a driver (not illustrated in the drawings), such as a motor, may be driven to inform that connecting with the processor 3 has completed.

At step S906, the display controller 584 causes the display unit 55 to display that it is not possible to connect with the processor 3. This allows the user to instinctively know that it is not possible to connect with the processor 3. After step S906, the terminal device 5 returns to the main routine in FIG. 7.

FIG. 7 will be referred back to continue describing step S703 and the following steps.

At step S703, when the terminal device 5 and the processor 3 are interactively communicating with each other (YES at step S703), the terminal device 5 moves to step S704. On the other hand, when the terminal device 5 and the processor 3 are not interactively communicating with each other (No at step S703), the terminal device 5 ends the process.

At step S704, when an audio command is input from the audio input unit 54 (YES at step S704), the communication controller 583 transmits, to the processor 3, the audio command that is input from the audio input unit 54 via the communication unit 51 (step S705). After step S705, the terminal device 5 moves to step S706 to be described below. On the contrary, when no audio command is input from the audio input unit 54 (NO at step S704), the terminal device 5 ends the process.

At step S706, in the case where the endoscopic image data is received from the processor 3 (YES at step S706), when tag information on the control content of the audio command is received from the processor 3 (YES at step S707), the recording controller 585 records the endoscopic image data and the tag information on the control content of the audio command in association with each other in the recorder 56 (step S708).

Based on the tag information that is received from the processor 3, the communication controller 583 acquires relevant image data from the server 200 via the communication unit 51 and the network N100 (step S709). The relevant image data herein refers to image data relevant to the tag information that is, for example, case image data, such as endoscopic image data obtained by capturing images of another subject after execution of the audio command. In this case, the recording controller 585 may cause the recorder 56 to record the relevant image data that is acquired by the communication controller 583 in association with the tag information and the endoscopic image data.

The display controller 584 then causes the display unit 55 to display an endoscopic image corresponding to the endoscopic image data and a relevant image corresponding to the relevant image data (step S710). In this case, when the endoscopic image data that is received by the communication unit 51 is video data that is sequentially transmitted, the display controller 584 sequentially updates the endoscopic image corresponding to the endoscopic image data chronologically. The display controller 584 causes the display unit 55 to display the endoscopic image and the relevant image such that the endoscopic image and the relevant image can be compared with each other. For example, the display controller 584 may cause the display unit 55 to display the endoscopic image and the relevant image in parallel, to make a display in which the relevant image that is reduced in size according to a given ratio is superimposed onto the endoscopic image, or to make a display in which the endoscopic image that is reduced in size according to a given ratio is superimposed onto the relevant image.

The communication controller 583 transmits the endoscopic image data, the tag information, and the result of verification performed by the verification unit 582 in association with one another to the server 200 via the communication unit 51 and the network N100 (step S711). After step S711, the terminal device 5 moves to step S713 to be described below.

At step S706, when the endoscopic image data is not received from the processor 3 (NO at step S706), the terminal device 5 moves to step S713 to be described below.

At step S707, when the tag information on the control content of the audio command is not received from the processor 3 (NO at step S707), the recording controller 585 records the endoscopic image data that is received from the processor 3 in the recorder 56 (step S712). After step S712, the terminal device 5 moves to step S713 to be described below.

At step S713, when an instruction signal to end operations of the endoscope system 1 while communication with the processor 3 is input from the operation unit 57 (YES at step S713), the terminal device 5 moves to step S714 to be described below. On the other hand, when no instruction signal to end operations of the endoscope system while communicating with the processor 3 is input from the operation unit 57 (NO at step S713), the terminal device 5 returns to step S704 described above.

At step S714, the recording controller 585 records the processor IP address of the processor 3 in the recorder 56. After step S714, the terminal device 5 ends the process.

According to the above-described first embodiment of the disclosure, in the case where the processor 3 and the terminal device 5 can communicate with each other, the setting unit 364 makes a setting such that the command content partly differs between the first audio command that is receivable by the processor 3 and the second audio command that is receivable by the terminal device 5 and accordingly it is possible to prevent an incorrect operation of the endoscope system 1.

According to the first embodiment of the disclosure, in the case where the processor 3 and the terminal device 5 can communicate with each other, when the processor 3 receives inputs of the first audio command and the second audio command from the terminal device 5, the selector 367 selects a priority audio command to be prioritized, which makes it possible to prevent an incorrect operation even when multiple audio commands are input.

According to the first embodiment of the disclosure, when the processor 3 receives inputs of the first audio command and the second audio command from the terminal device 5, the selector 367 selects a priority audio command to be prioritized based on the level of the operator of the endoscope 2 that is acquired by the acquisition unit 35 and the level of the user who uses the terminal device 5, which makes it possible to assuredly prevent an incorrect operation.

According to the first embodiment of the disclosure, based on the level that is assigned to the user of the terminal device 5 on which verification is performed by the verification unit 582, the setting unit 364 sets multiple peripherals that are operable by the terminal device 5 according to the second audio command, which makes it possible to prevent the peripherals from being operated by mistake.

According to the first embodiment of the disclosure, when the first audio command or the second audio command serves as an instruction to record the endoscopic image data, the communication controller 363 causes the communication unit 32 to transmit the endoscopic image data to the terminal device 5, which allows the operator to check the condition of the subject, such as a patient, during the operation on the terminal device 5.

According to the first embodiment of the disclosure, the communication controller 363 transmits the tag information on the content of the first audio command or the second audio command and the endoscopic image data in association with each other to the terminal device 5, which makes it possible to easily search for the endoscopic image data using the tag information after the operation on the subject.

According to the first embodiment of the disclosure, the display controller 584 causes the display unit 55 to display the endoscopic image corresponding to the endoscopic image data per set of tag information on the content of the first audio command or the second audio command, which makes it possible to check a list of the group of endoscopic images each of which is associated with each set of tag information.

According to the first embodiment of the disclosure, the communication controller 583 acquires the relevant image data that is recorded in the server 200 based on the tag information and the display controller 584 causes the display unit 55 to display the endoscopic image and the relevant image, which makes it possible to view the endoscopic image and the relevant image in comparison with each other.

According to the first embodiment of the disclosure, the communication controller 583 transmits the result of verification performed by the verification unit 582, the tag information on the content of the second audio command, and the endoscopic image data in association with one another to the server 200 that is connected with the network N100, which makes it possible to easily search for the endoscopic image data using the tag information after the operation on the subject.

Second Embodiment

A second embodiment of the disclosure will be described. In the above-described first embodiment, the processor 3 sets peripherals that are operable according to the audio command based on the level of the registered user of the terminal device 5. In the second embodiment, the terminal device sets peripherals that are operable according to the audio command based on the level of the registered user. After a configuration of an endoscope system according to the second embodiment is described, each of processes executed by a processor and a terminal device will be described. The same components as those of the endoscope system according to the above-described first embodiment are denoted by the same reference numbers as those of the first embodiment and description thereof will be omitted.

Configuration of Endoscope System

Figure 10:
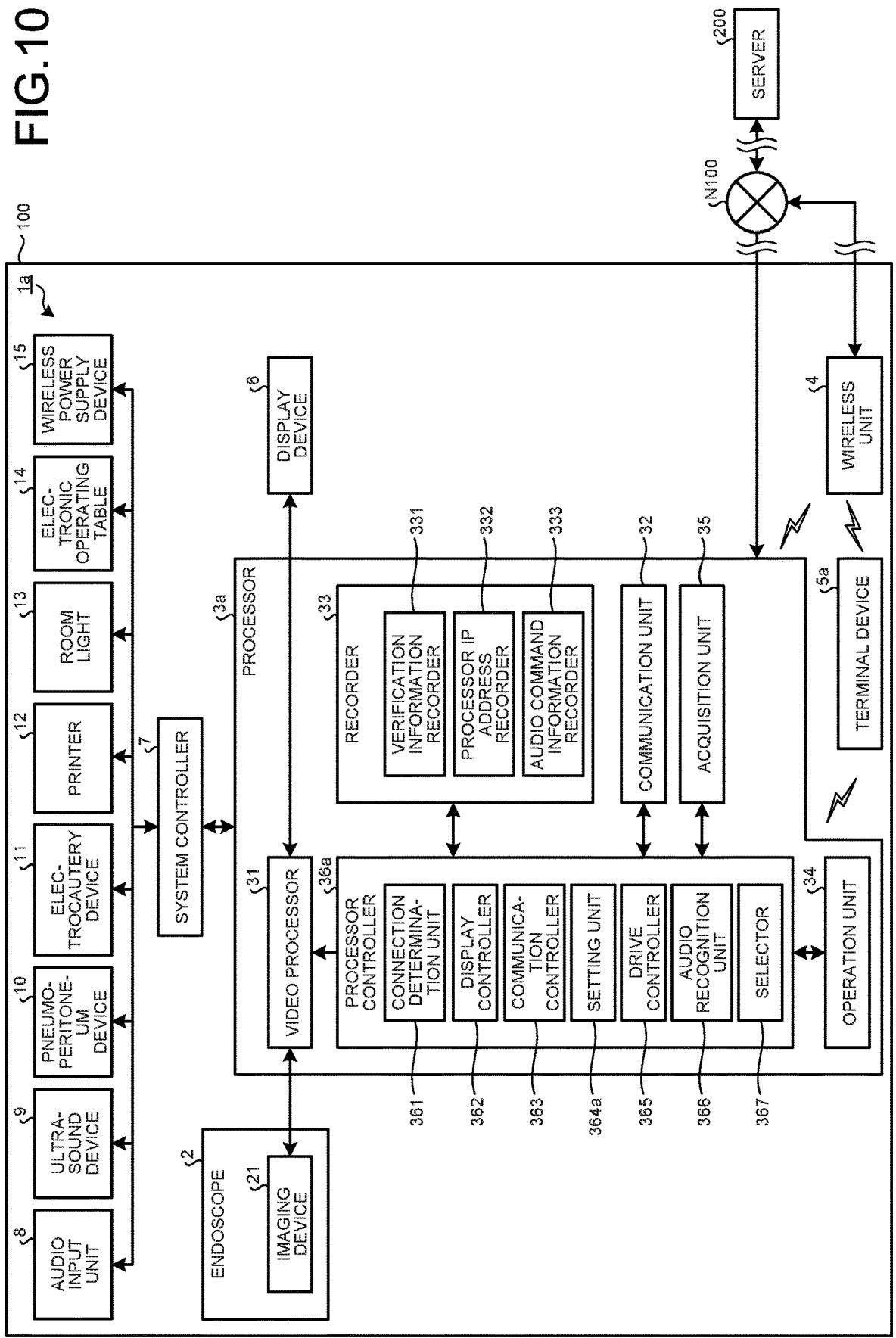
FIG. 10 is a block diagram illustrating a functional configuration of an endoscope system according to a second embodiment of the disclosure.

FIG. 10 is a block diagram illustrating a functional configuration of an endoscope system according to the second embodiment of the disclosure. An endoscope system 1a illustrated in FIG. 10 includes a processor 3a and a terminal device 5a instead of the processor 3 and the terminal device 5 of the endoscope system 1 according to the above-described first embodiment.

Configuration of Processor

The processor 3a includes a processor controller 36a instead of the processor controller 36 of the processor 3 according to the above-described first embodiment. The processor controller 36a includes a setting unit 364a instead of the setting unit 364 of the processor controller 36 according to the above-described first embodiment.

Based on an operator ID that is acquired by the acquisition unit 35 and verification information that is recorded in the verification information recorder 331, the setting unit 364a sets multiple peripherals that are operable according to a first audio command that is received by the audio input unit 8 via the system controller 7.

Configuration of Terminal Device

Figure 11:
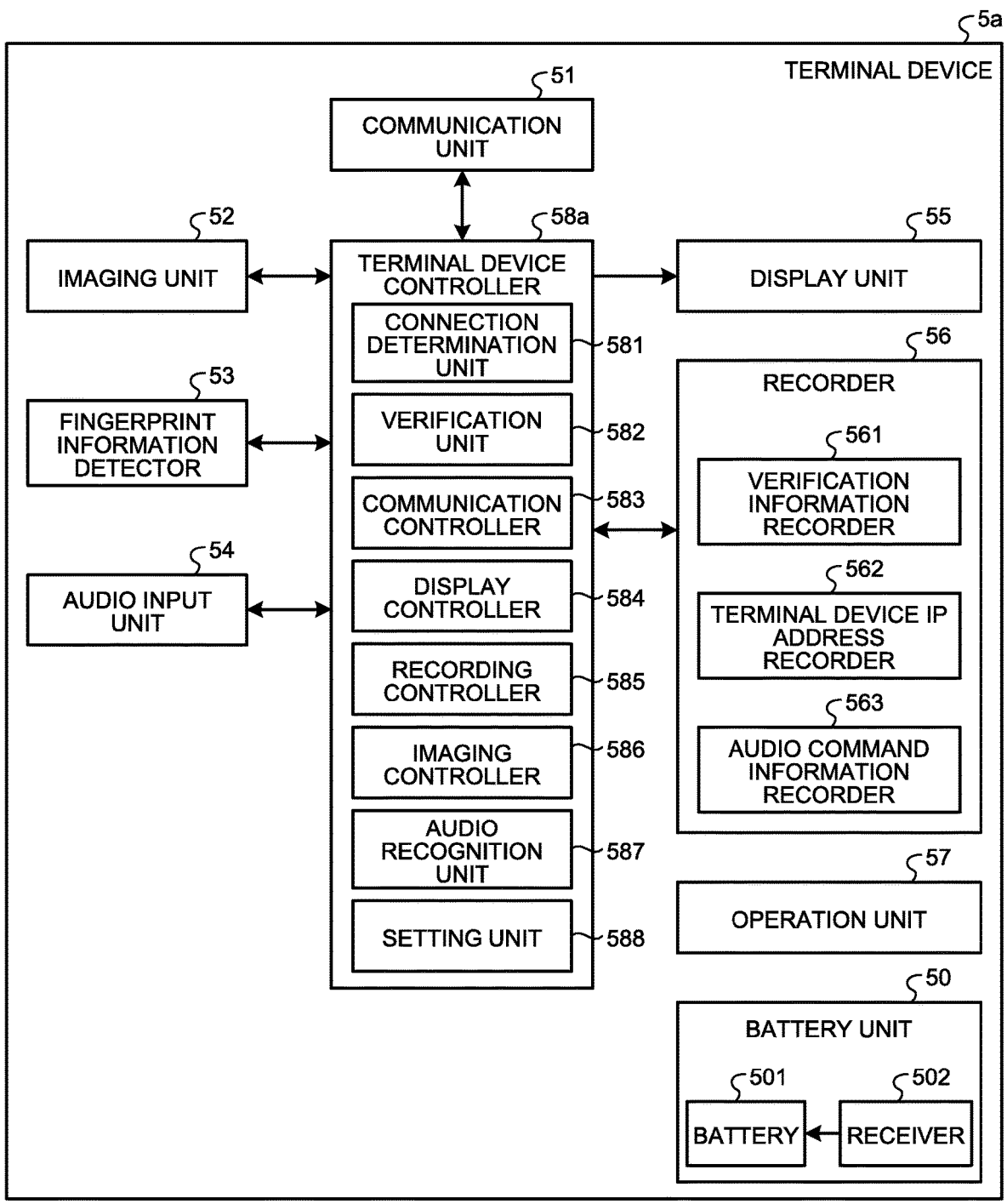
FIG. 11 is a block diagram illustrating a functional configuration of a terminal device according to a second embodiment of the disclosure.

A configuration of the terminal device 5a will be described. FIG. 11 is a block diagram illustrating a functional configuration of the terminal device 5a. The terminal device 5a illustrated in FIG. 11 includes a terminal device controller 58a instead of the terminal device controller 58 of the terminal device 5 according to the above-described first embodiment. The terminal device controller 58a further includes a setting unit 588 in addition to the configuration of the terminal device controller 58 according to the above-described first embodiment.

Based on a level that is assigned to a registered user corresponding to a result of verification performed by the verification unit 582 and verification information that is recorded in the verification information recorder 331, the setting unit 588 sets multiple peripherals that are operable according to a second audio command via the system controller 7.

Process Executed by Processor

Figure 12:
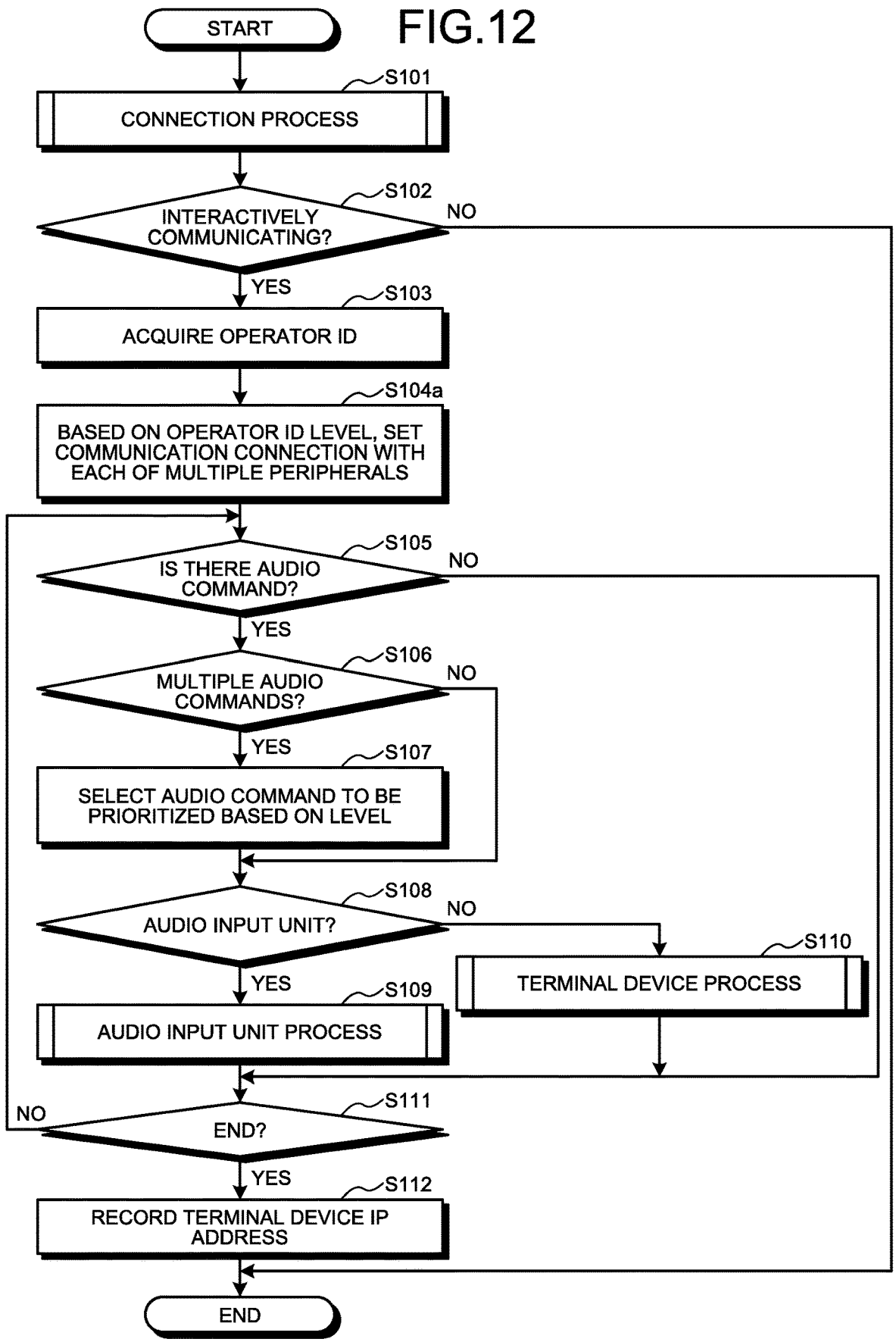
FIG. 12 is a flowchart illustrating an overview of a process that is executed by a processor according to the second embodiment of the disclosure.

A process that is executed by the processor 3a will be described. FIG. 12 is a flowchart illustrating an overview of the process that is executed by the processor 3a. The processor 3a executes the same process as the process described in the above-described first embodiment and executes step S104a instead of step S104. Step S104a will be thus described below.

At step S104a, based on an operator ID level that is acquired by the acquisition unit 35, the setting unit 364a sets communication connection with each of the peripherals that are operable according to an audio command that is received by the audio input unit 8 via the system controller 7. After step S104a, the processor 3a moves to step S105.

Process Executed by Terminal Device

A process executed by the terminal device 5a will be described. The terminal device 5a executes a process similar to the process executed by the terminal device 5 according to the above-described first embodiment and only the verification process differs. The verification process that is executed by the terminal device 5a will be thus described below.

Verification Process

Figure 13:
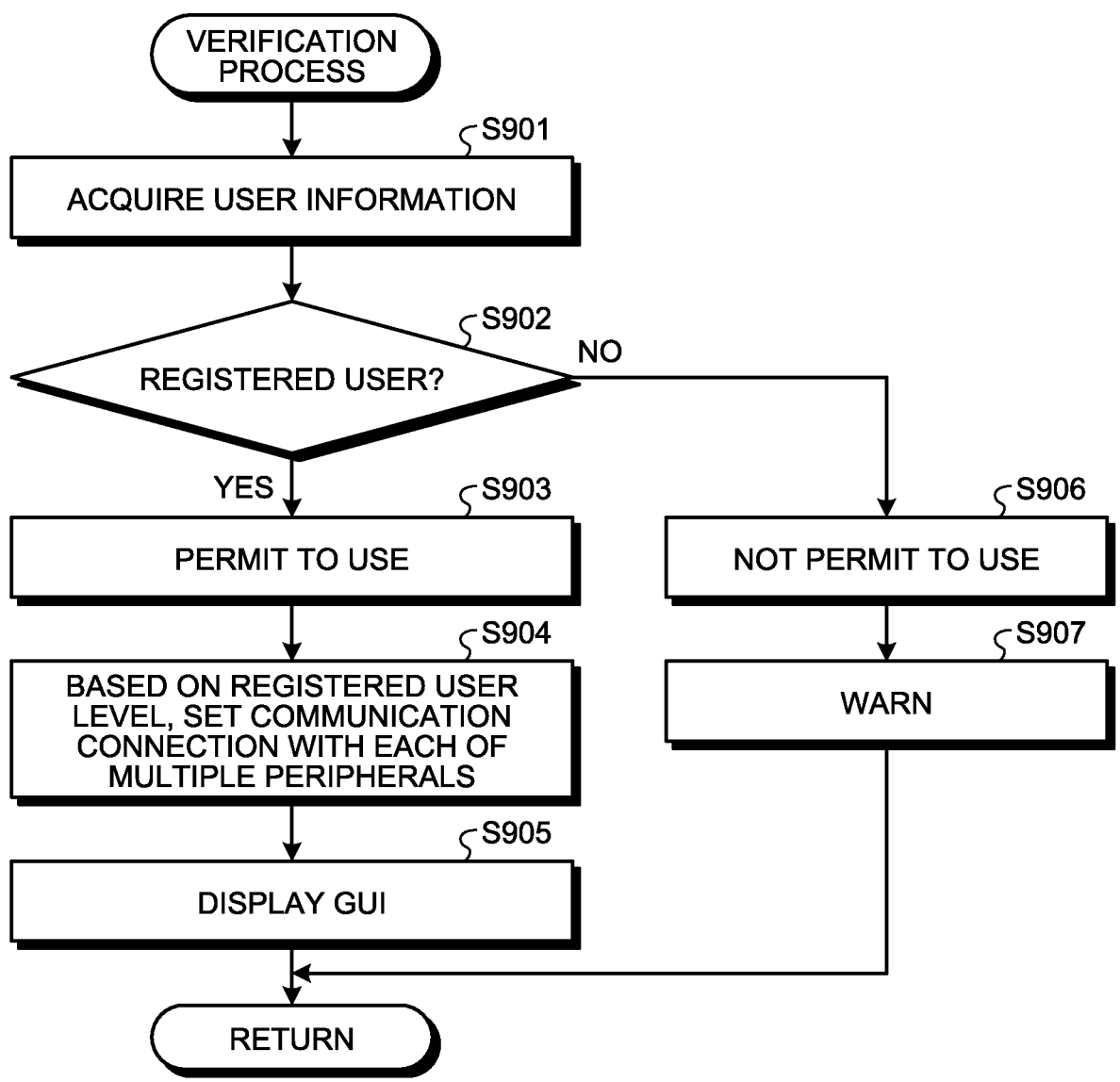
FIG. 13 is a flowchart illustrating a verification process that is execute by the terminal device according to the second embodiment of the disclosure.

FIG. 13 is a flowchart illustrating an overview of the verification process that is executed by the terminal device 5a. In FIG. 13, steps S901 to S903 respectively correspond to steps S801 to S803 in FIG. 8 described above.

At step S904, based on the level that is assigned to the registered user corresponding to the result of verification performed by the verification unit 582 and the verification information that is recorded in the verification information recorder 331, the setting unit 588 sets each of multiple peripherals operable according to a second audio command via the system controller 7.

The display controller 584 causes the display unit 55 to display a GUI, or the like, of the peripherals that are operable by the audio command that are set by the setting unit 588 (step S905). After step S905, the terminal device 5a returns to the main routine in FIG. 7 described above.

Steps S906 and S907 correspond respectively to steps S805 and S806 in FIG. 8 described above. After step S907, the terminal device 5a returns to the main routine in FIG. 7.

According to the second embodiment of the disclosure described above, the setting unit 588 sets the peripherals that are operable according to the second audio command via the system controller 7 based on the level that is assigned to the user of the terminal device 5a on which verification is performed by the verification unit 582, which makes it possible to prevent an incorrect operation.

Other Embodiments

It is possible to form various embodiments by appropriately combining multiple components disclosed in the above-described embodiment of the disclosure. For example, some components may be omitted from all the components described in the embodiment of the disclosure described above. Components described in the embodiment of the disclosure described above may be combined appropriately.

In the embodiment of the disclosure, the light source device is arranged in the processor. Alternatively, the light source may be arranged separately.

The embodiment of the disclosure employs an endoscope system. Alternatively, a capsule endoscope, a video microscope that captures images of a subject, a mobile phone with an imaging function, or a tablet terminal device with an imaging function may be employed.

The embodiment of the disclosure employs an endoscope system including a medical endoscope. Alternatively, an endoscope system including an industrial endoscope may be employed.

In the embodiment of the disclosure, "-er" or "unit" described herein may be read as "means" or "circuitry". For example, the controller may be read as a control means or a control circuitry.

A program to be executed for the embodiment of the disclosure is recorded in an installable or executable file data in a computer-readable recording medium, such as a CD-ROM, a flexible disk (FD), a CD-R, a digital versatile disk (DVD), a USD medium, or a flash memory and is provided.

The program that is executed for the embodiment of the disclosure may be configured such that the program is stored in a computer that is connected to a network, such as the Internet, and is downloaded and provided. Furthermore, the program to be executed for the embodiment of the disclosure may be configured to be provided or distributed via a network, such as the Internet.

In the description of the flowcharts herein, the context of the process among steps is clearly specified using expressions including "first of all", "then", or "subsequently"; however, the order of the processes necessary to implement the disclosure is not uniquely determined by those expressions. In other words, the process order of the flowcharts described herein is changeable within a range causing no inconsistency. The embodiment is not limited to the program including simple branches, and the program may be branched off according to general determination on more determination items. In that case, the technology of artificial intelligence that performs machine learning while repeating learning by inducing the user to perform manual operations may be used together. The artificial intelligence may be implemented in a manner that the artificial intelligence is caused to learn operation patterns performed by many specialists and perform deep learning such that more complicated conditions are incorporated.

The disclosure achieves an effect that, even when multiple audio input units are used, it is possible to prevent an incorrect operation.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
a processor configured to perform image processing on endoscopic image data that is acquired by an endoscope that performs in-vivo observation on a subject, the processor being connectable with multiple peripherals, the processor being configured to receive an input of a first audio command serving as an instruction to drive any one of the peripherals based on audio data that is generated by an audio input circuit receiving an input of sound;
a terminal device configured to wirelessly communicate with the processor and receive an input of a second audio command serving as an instruction to drive any one of the peripherals using sound;
a setting circuit configured to, in a case where the processor and the terminal device can communicate with each other, make a setting such that the first audio command that is receivable by the processor and the second audio command that is receivable by the terminal device differ from each other at least partly; and
a first communication controller configured to, when the first audio command or the second audio command serves as an instruction to record the endoscopic image data, transmit the endoscopic image data to the terminal device.

2. The endoscope system according to claim 1, further comprising:
a selector configured to select a priority audio command to be prioritized when the processor receives inputs of the first audio command and the second audio command from the terminal device in the case where the processor and the terminal device can communicate with each other; and
a drive controller configured to drive any one of the peripherals based on the priority audio command that is selected by the selector.

3. The endoscope system according to claim 2, further comprising:
an acquisition circuit configured to acquire operator identification information that identifies an operator of the endoscope; and
a recorder configured to record multiple sets of the operator identification information in association with levels according to which operating each of the peripherals is permitted,
wherein the selector is configured to, when the processor receives the inputs of the first audio command and the second audio command from the terminal device, select the priority audio command based on a level of the operator that is acquired by the acquisition circuit and on a level of a user who uses the terminal device.

4. The endoscope system according to claim 1, further comprising a system controller that is connected to the processor and each of the peripherals, the system controller being configured to control driving the peripherals, wherein the terminal device further includes a verification circuit configured to verify whether a user of the terminal device is a registered user who is registered previously, and the processor includes a drive controller configured to drive any one of the peripherals based on the first audio command or the second audio command; and the setting circuit, the setting circuit is configured to, based on a level that is assigned to the user on which verification is performed by the verification circuit, set the peripherals that are operable by the terminal device according to the second audio command via the system controller, and the drive controller is configured to disable the second audio command that is input from the terminal device when the setting circuit does not make a setting such that the peripherals corresponding to the second audio command that is input from the terminal device are operable.

5. The endoscope system according to claim 1, further comprising a system controller that is connected to the processor and each of the peripherals, the system controller being configured to control driving the peripherals, wherein the terminal device further includes a verification circuit configured to verify whether a user of the terminal device is a registered user who is registered previously; and the setting circuit, and the setting circuit is configured to, based on a level that is assigned to the user on which verification is performed by the verification circuit, set the peripherals that are operable according to the second audio command via the system controller.

6. The endoscope system according to claim 1, wherein the processor includes the first communication controller, and the first communication controller is configured to transmit, to the terminal device, tag information on content of the first audio command or the second audio command and the endoscopic image data in association with each other.

7. The endoscope system according to claim 6, wherein the terminal device further includes a display configured to display an image; and a display controller configured to control a display mode of the display, and the display controller is configured to cause the display to display an endoscopic image corresponding to the endoscopic image data for each set of the tag information.

8. The endoscope system according to claim 7, further comprising a server that is connected to the terminal device and the processor via a network, the server being configured to record relevant image data that is relevant to the endoscopic image, wherein the terminal device further includes a second communication controller configured to acquire the relevant image data that is recorded in the server based on the tag information, and the display controller is configured to cause the display to display the endoscopic image and a relevant image corresponding to the relevant image data.

9. The endoscope system according to claim 1, wherein the terminal device further includes a record controller configured to record the second audio command of which input is received by the terminal device and the endoscopic image data in association with each other in a recorder.

10. The endoscope system according to claim 4, wherein the terminal device further includes a second communication controller configured to transmit a result of verification performed by the verification circuit, tag information on content of the second audio command, and the endoscopic image data in association with each other to a server that is connected to a network.

11. The endoscope system according to claim 1, wherein the first audio command is configured of a command according to which all the peripherals are operable, and the second audio command is configured of a command according to which a peripheral not directly relevant to an operation is operable.

12. A control method that is executed by an endoscope system including a processor configured to perform image processing on endoscopic image data that is acquired by an endoscope that performs in-vivo observation on a subject, the processor being connectable with multiple peripherals, the processor being configured to receive an input of a first audio command serving as an instruction to drive any one of the peripherals based on audio data that is generated by an audio input circuit receiving an input of sound; and a terminal device configured to wirelessly communicate with the processor and receive an input of a second audio command serving as an instruction to drive any one of the peripherals using sound, the control method comprising:

in a case where the processor and the terminal device can communicate with each other, making a setting such that the first audio command that is receivable by the processor and the second audio command that is receivable by the terminal device differ from each other at least partly; and when the first audio command or the second audio command serves as an instruction to record the endoscopic image data, transmit the endoscopic image data to the terminal device.

* * * * *